US012618990B2

(12) United States Patent
　　Fujii

(10) Patent No.: US 12,618,990 B2
(45) Date of Patent: May 5, 2026

(54) RADIATION IMAGE SCANNER

(71) Applicant: J. MORITA MFG. CORP., Kyoto (JP)

(72) Inventor: Yusuke Fujii, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 225 days.

(21) Appl. No.: 18/614,113

(22) Filed: Mar. 22, 2024

(65) Prior Publication Data

US 2024/0319390 A1 Sep. 26, 2024

(30) Foreign Application Priority Data

Mar. 23, 2023 (JP) ................................. 2023-046780

(51) Int. Cl.
　　*G01T 7/00* (2006.01)
　　*G01T 1/16* (2006.01)
　　*A61B 5/00* (2006.01)
(52) U.S. Cl.
　　CPC .................. *G01T 7/00* (2013.01); *G01T 1/16* (2013.01); *A61B 5/0062* (2013.01)
(58) Field of Classification Search
　　CPC ............ G01T 7/00; G01T 1/16; A61B 5/0062
　　See application file for complete search history.

(56) References Cited

U.S. PATENT DOCUMENTS

| | | | |
|---|---|---|---|
| 4,864,135 A | 9/1989 | Kato et al. | |
| 4,900,926 A * | 2/1990 | Yoshimura | G03B 42/02 250/589 |
| 2010/0171052 A1* | 7/2010 | Thoms | H04N 1/04 250/584 |
| 2011/0049373 A1 | 3/2011 | Sugihara et al. | |

FOREIGN PATENT DOCUMENTS

| | | |
|---|---|---|
| EP | 4 589 341 A1 | 7/2025 |
| JP | 1-94335 A | 4/1989 |
| JP | 4-320250 A | 11/1992 |
| JP | 2011-53459 A | 3/2011 |

OTHER PUBLICATIONS

Extended European Search Report issued Jul. 10, 2024 in European Patent Application No. 24163804.8, 7 pages.
Office Action dated Mar. 12, 2026, issued in counterpart EP Application No. 24163804.8, (7 pages).

* cited by examiner

*Primary Examiner* — Hugh Maupin
(74) *Attorney, Agent, or Firm* — Oblon, McClelland, Maier & Neustadt, L.L.P.

(57) ABSTRACT

A radiation image scanner is a radiation image scanner that reads a radiation image from a front surface of an image plate (IP), and includes a stage that supports the IP from a back surface side and a setting guide including a first IP guide surface that guides the IP obliquely downward. At least one of the setting guide and the stage includes an inclined surface (second IP guide surface), which is a surface inclined downward to the opposite side with respect to the first IP guide surface, receives the IP guided by the first IP guide surface, and guides the IP obliquely downward. At least one of the stage and the setting guide includes a front-back inverting portion that comes into contact with the IP from a front surface side of the IP to invert the IP to the same inclined posture as the inclined surface.

18 Claims, 23 Drawing Sheets

F I G. 3
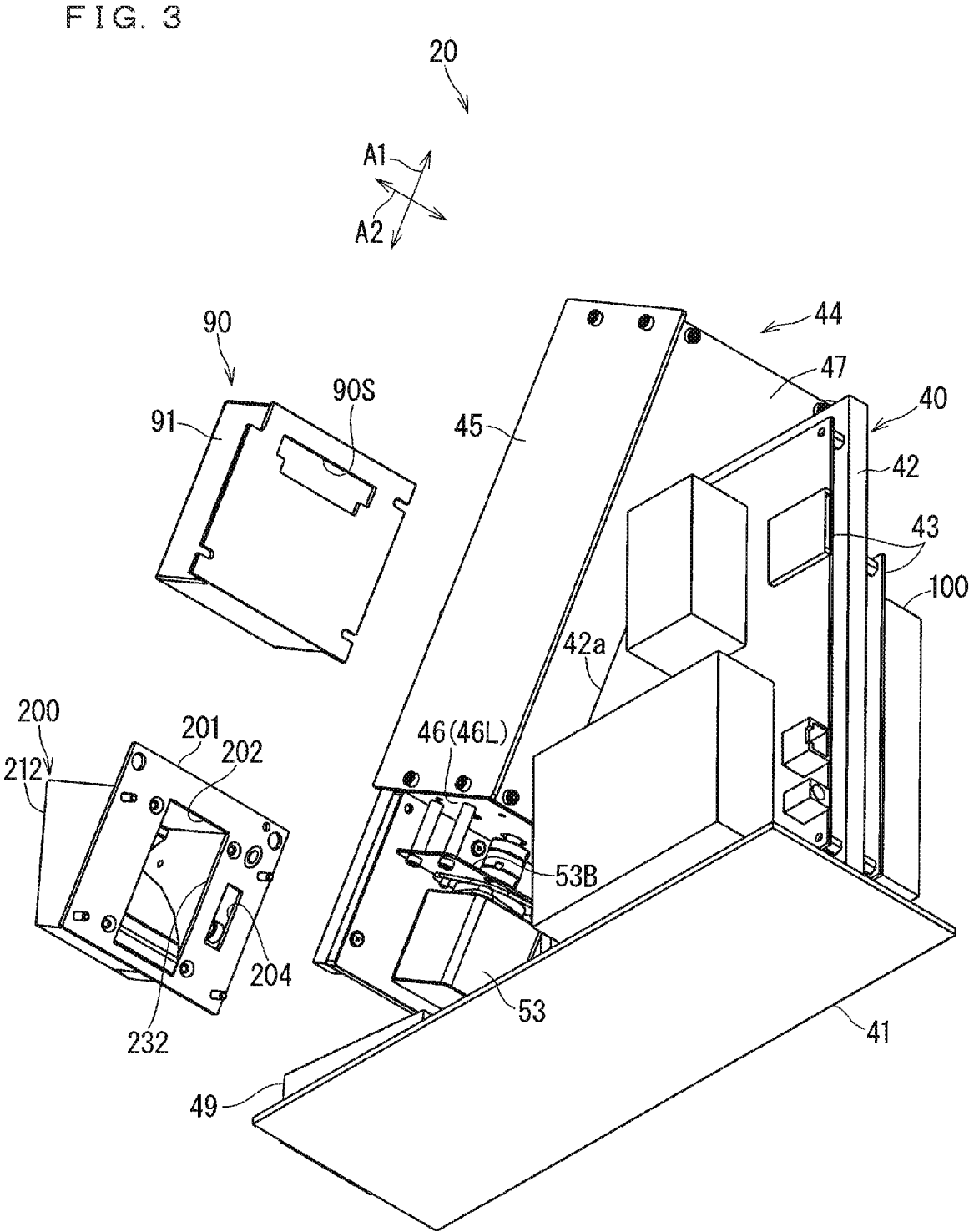

F I G. 5
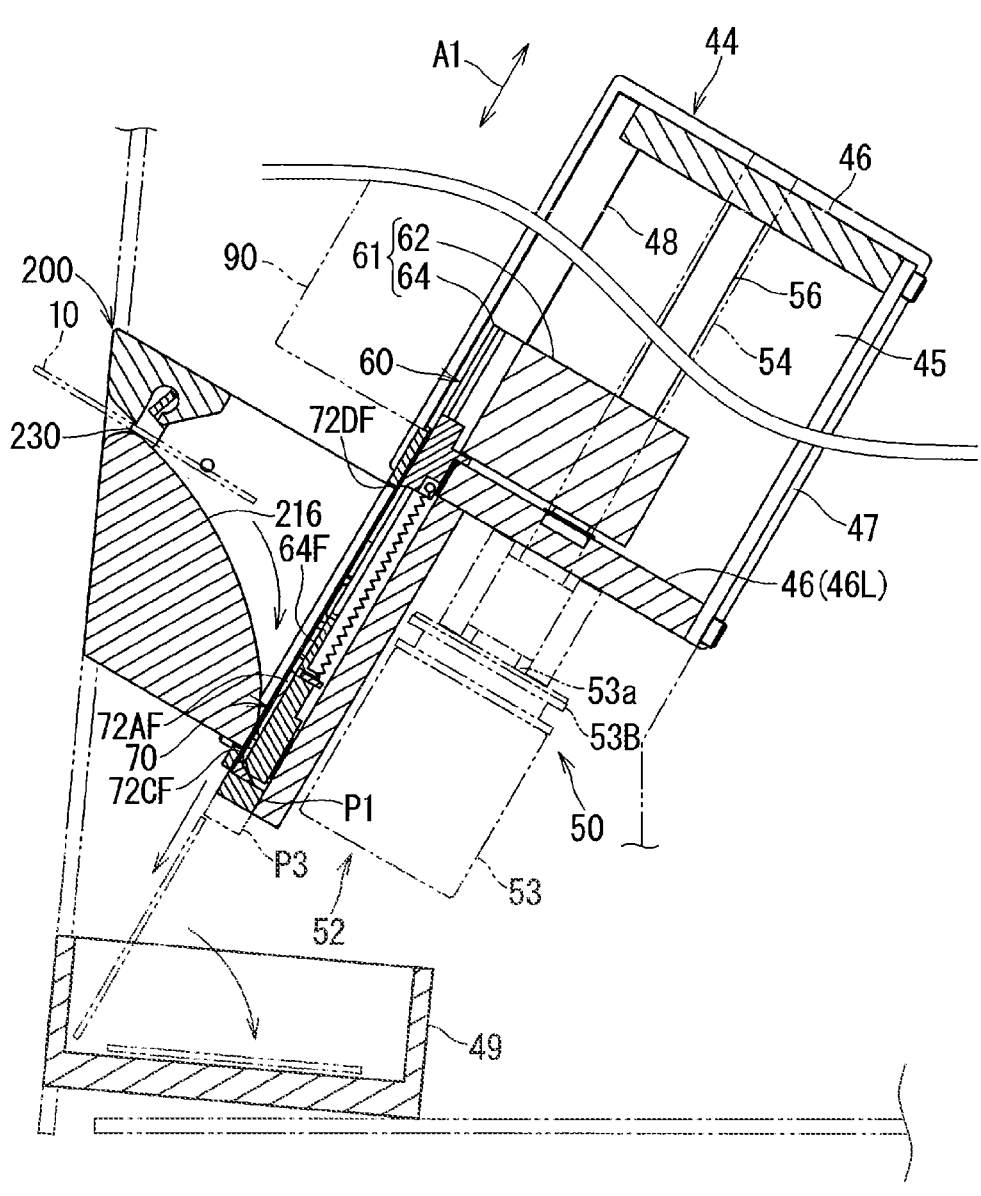

F I G. 10
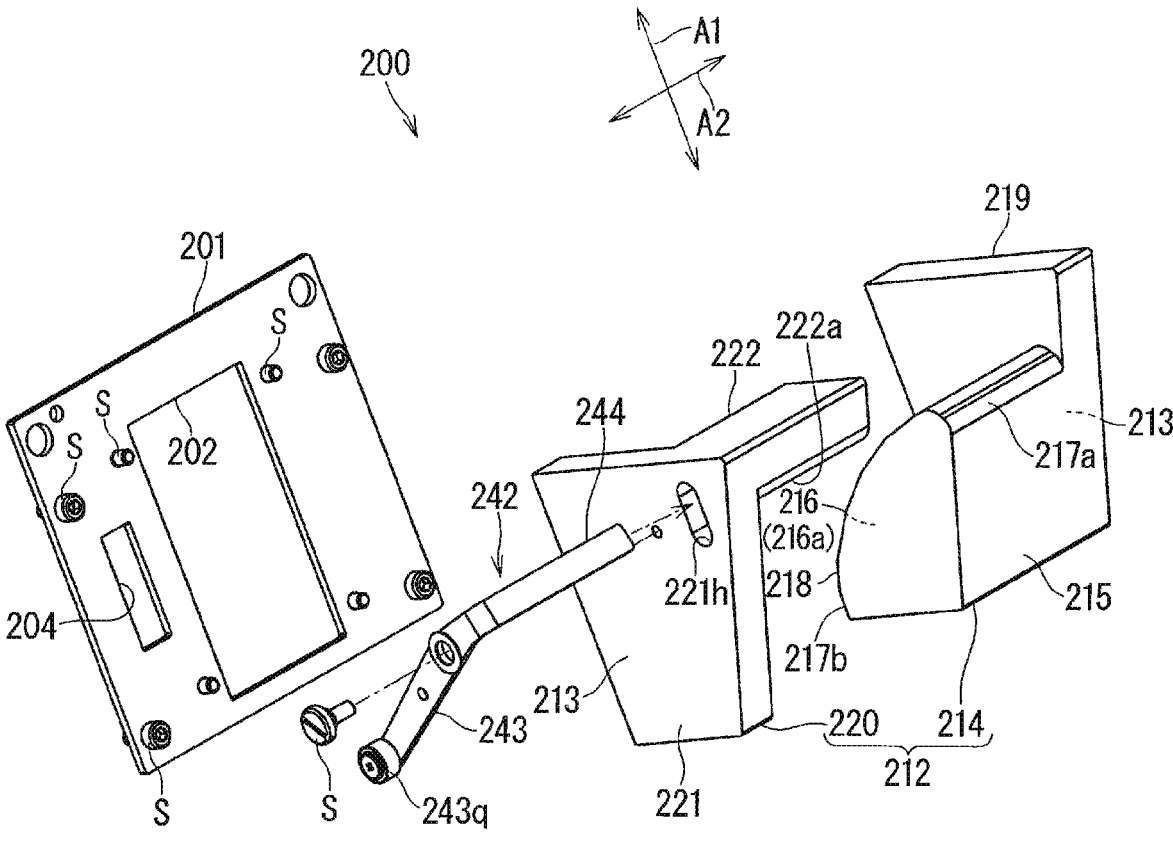

30

222  200
222bg
10  10b    10    212
Q2 Q1    244
11(10a)    222a    222b  221    201
230    W    221h    202
217a    10    Q3    216(216a)    10    232
Q4
Q5    10
11(10a)    10b
64
64F
60
31
215    218
217b
72C    72CF
L1    L2
D

UPWARD
A1
DOWNWARD 10    416A    416Ag

F I G. 1 7
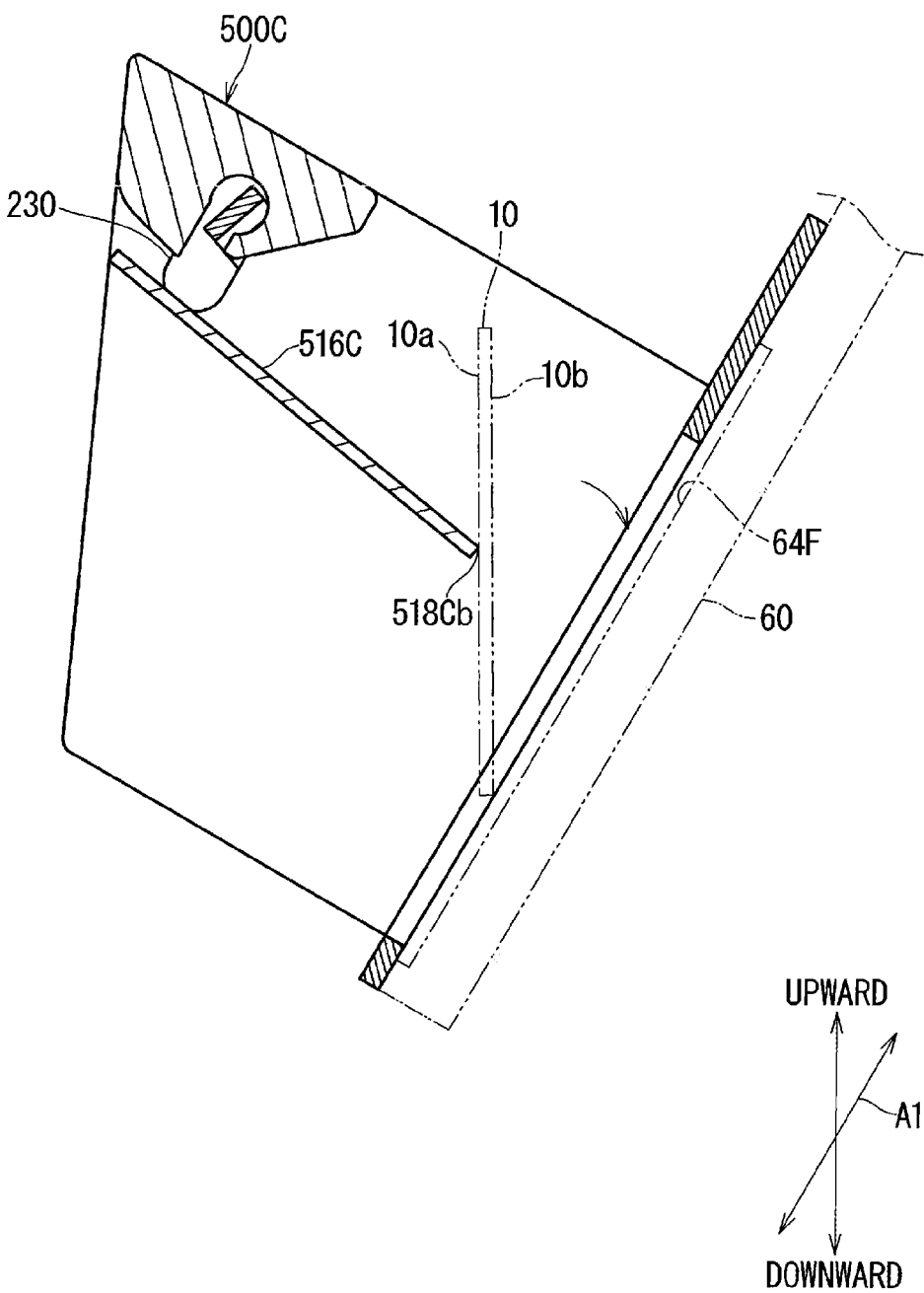

RADIATION IMAGE SCANNER

BACKGROUND OF THE DISCLOSURE

Field of the Disclosure

The present disclosure relates to a radiation image scanner.

Description of the Background Art

Japanese Patent Publication No. 2011-53459 discloses a radiation image scanner including a conveyance mechanism that conveys an IP (imaging plate). The conveyance mechanism including a belt that holds an IP and a belt drive mechanism that rotates the belt is disclosed as an example. The IP is conveyed while placed on a holding surface that is a part of the belt.

In the technique disclosed in Patent Document 1, the IP is inserted into an inlet formed in a housing while a radiation image forming surface faces upward, and is placed on a holding surface of a belt.

For this reason, when the IP is inserted into the inlet, the radiation image forming surface facing upward may be exposed to light outside the scanner. When the radiation image forming surface is exposed to external light, the radiation image forming surface emits light, energy stored in the radiation image forming surface is released and dissipated, and a part of image data may be lost.

SUMMARY

An object is to make the radiation image forming surface of the IP less likely to be exposed to external light when the IP is set in the radiation image scanner.

A radiation image scanner is a radiation image scanner that reads a radiation image from a front surface of an imaging plate (IP), the radiation image scanner including: a stage that supports the IP from a back surface side; an excitation light source that irradiates the IP supported by the stage with excitation light; a photodetector that detects light emitted from the IP by the excitation light; and a setting guide that guides the IP toward the stage, the setting guide including an first IP guide surface that guides the IP obliquely downward, the first IP guide surface being inclined downward, wherein at least one of the setting guide and the stage include a second IP guide surface being inclined downward, the second IP guide surface is a surface that is inclined downward to an opposite side with respect to the first IP guide surface, receives the IP guided by the first IP guide surface, and guides the IP obliquely downward, and at least one of the stage and the setting guide include a front-back inverting portion that inverts the IP in an inclined attitude identical to the second IP guide inclined surface while coming into contact with the IP guided by the second IP guide surface from a front surface side of the IP.

According to the radiation image scanner, the radiation image forming surface of the IP can be hardly exposed to external light when the IP is set in the radiation image scanner.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 2 and 3 are partially exploded perspective views illustrating the scanner;

FIG. 5 is a sectional view taken along a line V-V in FIG. 4;

FIG. 10 is an exploded perspective view illustrating the setting guide;

FIG. 17 is a sectional view illustrating a setting guide according to a fifth modification;

DESCRIPTION OF THE EMBODIMENTS

First Embodiment

<Entire Configuration>

Figure 1:
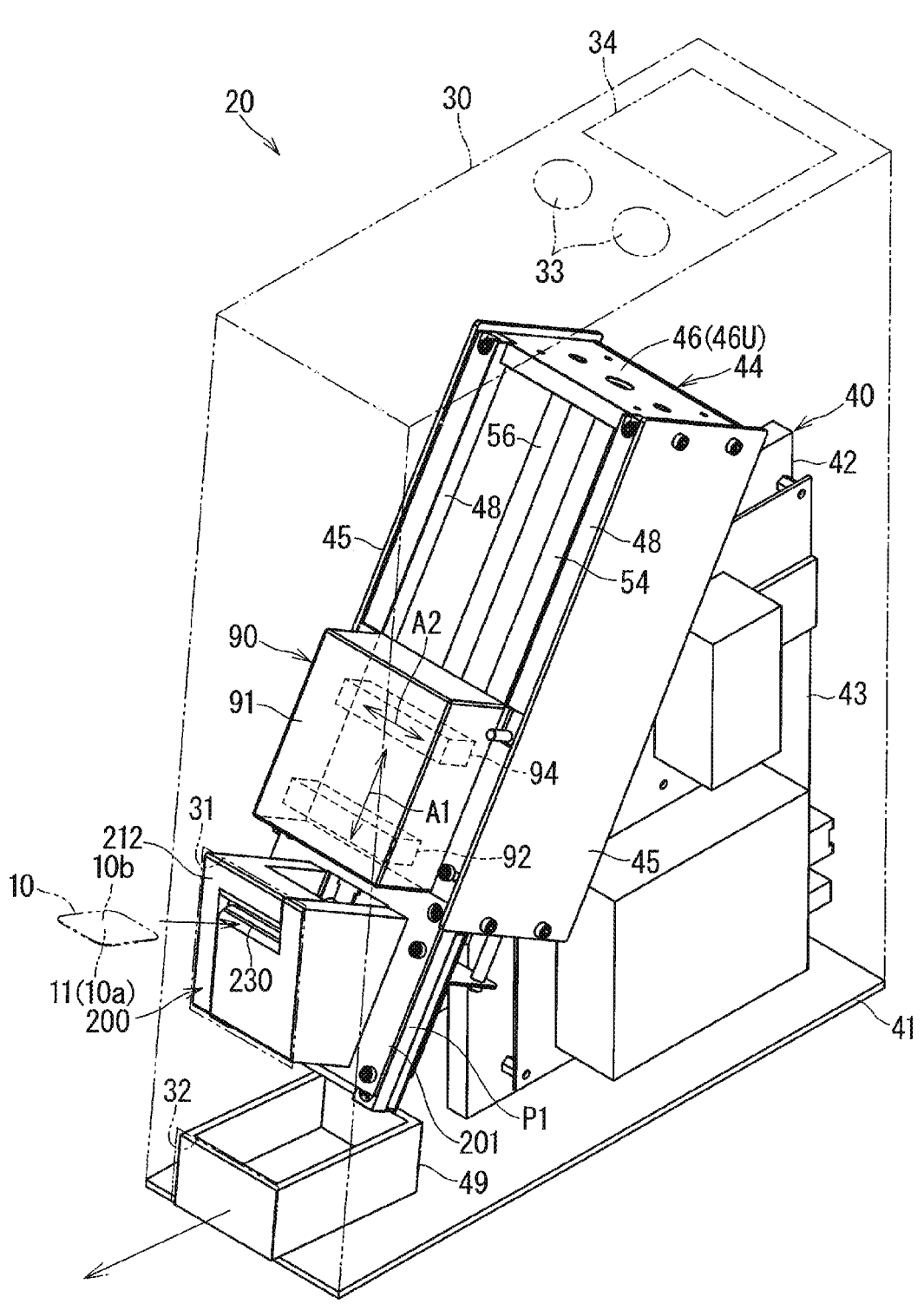
FIG. 1 is a schematic perspective view illustrating a scanner according to a first embodiment.
Figure 2:
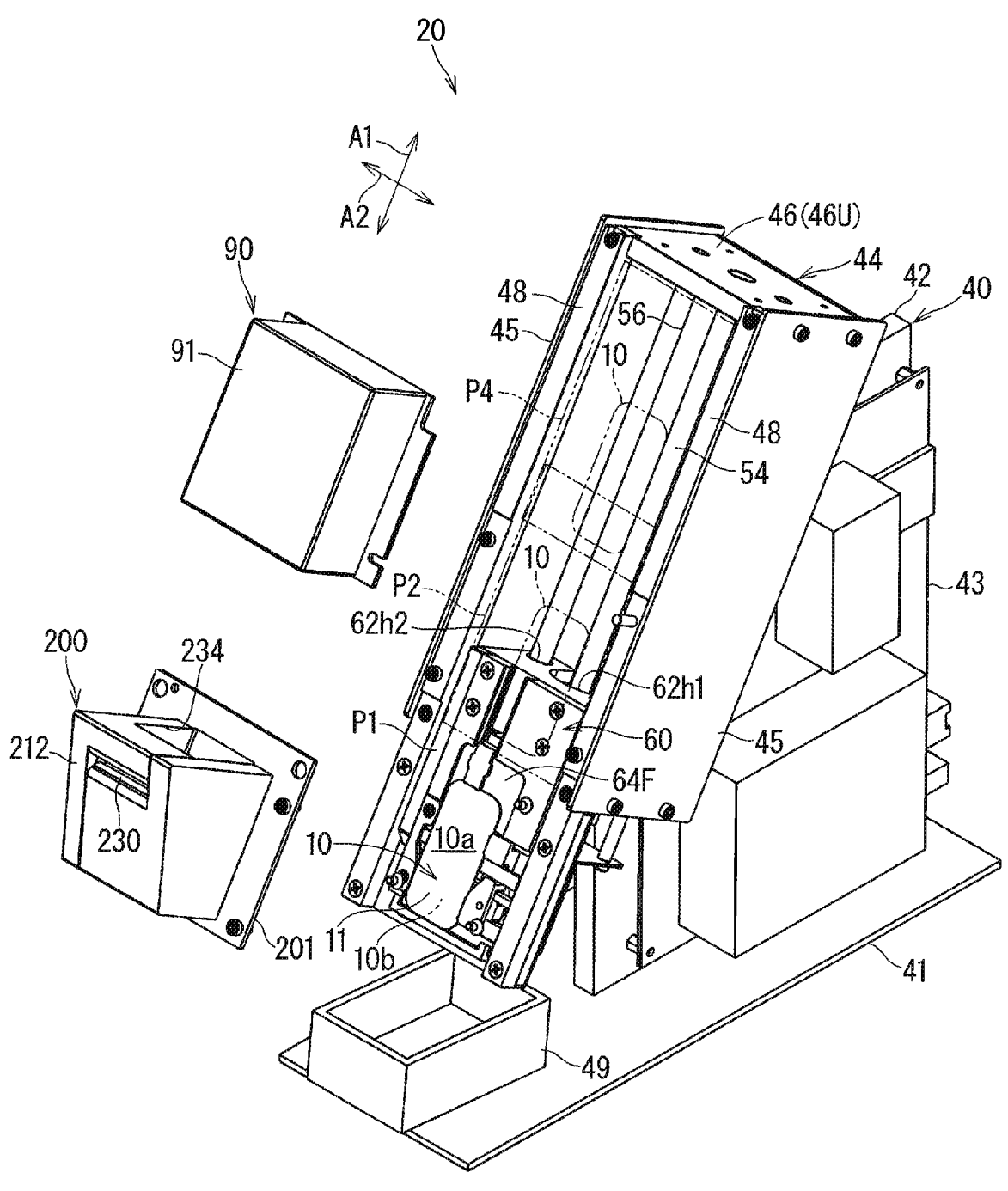

A radiation image scanner according to a first embodiment will be described below. FIG. 1 is a schematic perspective view illustrating a scanner 20. In FIG. 1, a housing 30 is indicated by a two-dot chain line. FIGS. 2 and 3 are partially exploded perspective views illustrating the scanner 20. In FIGS. 1 to 3, a stage 60 is located at a setting position P1. In FIGS. 2 and 3, a setting guide 200 and a reading unit 90 are disassembled. In FIG. 2, a reading position P2 and an inner side position P4 of the stage 60 inside the setting position P1 are indicated by two-dot chain lines.

The radiation image scanner 20 is a device that reads a radiation image from a front surface 10a of an imaging plate (IP) 10. In this application, the imaging plate is the IP.

The IP 10 has a flat shape including a radiation image forming layer 11, and is a storage medium that stores the radiation image. The radiation image forming layer 11 is exposed on a side of the front surface 10a of the IP 10. The radiation image forming layer 11 is a layer that accumulates energy of the emitted radiation and emits emission light corresponding to the accumulated energy. For example, the radiation image forming layer 11 is formed by applying a stimulable phosphor to one surface of a film formed of resin. When an X-ray from an X-ray generator is applied to the IP 10 through a capturing object, the energy corresponding to intensity of the X-ray is accumulated in the radiation image forming layer 11. Because the intensity of the X-ray is based on a distribution of an X-ray absorption region in the capturing object, the distribution of the energy accumulated in the radiation image forming layer 11 is the radiation image of the capturing object by the X-ray. In this manner, the IP 10 stores a radiation image by X-rays as a latent image.

The scanner 20 is a device that reads the radiation image from the radiation image forming layer 11 to generate image data of the radiation image. The scanner 20 includes a stage 60, an excitation light source 92, a photodetector 94, and the setting guide 200. The stage 60 supports the IP 10 from a side of a back surface 10b. The IP 10 held by the stage 60 is irradiated with excitation light from the excitation light source 92. When the IP 10 is irradiated with the excitation light, the radiation image forming layer 11 of the IP 10 emits light. The photodetector 94 detects the emission light. The image data of the radiation image is generated based on a detection signal of the photodetector 94.

The setting guide 200 is a guide that guides the IP 10 supplied from an outside of the scanner 20 toward the stage 60. A user of the scanner 20 can set the IP 10 on the stage 60 in a posture suitable for reading by supplying the IP 10 to the setting guide 200.

The front surface 10a of the IP 10 on which the radiation image forming layer 11 is formed may be regarded as a radiation image forming surface or an excitation light irradiation surface. The back surface 10b opposite to the front surface may be regarded as a contact surface that faces a supporting surface 64F of the stage 60 and is in contact with the supporting surface 64F. The back surface 10b is a surface opposite to the surface irradiated with the excitation light and is a surface opposite to the radiation image forming layer 11. When the IP 10 is correctly set on the stage 60 with respect to the front and back surfaces, the surface of the IP 10 facing the supporting surface 64F is a storage surface capable of storing the latent image and is a reading surface from which the stored latent image is read.

A configuration of each portion of the scanner 20 will be described.

<Housing>

The scanner 20 includes a housing 30 (see FIG. 1), and the stage 60, the excitation light source 92, the photodetector 94, and the setting guide 200 are housed in the housing 30.

The housing 30 includes an opening 31. For example, the opening 31 is formed on one of side surfaces around the housing 30. The opening 31 is formed in a shape that allows a portion of the setting guide 200 where an insertion port 230 is formed to be exposed to the outside. In the first embodiment, the opening 31 is formed in a square shape that exposes the entire outward surface of the setting guide 200 where the insertion port 230 is formed to the outside. The opening may have a shape that exposes only the insertion port 230 to the outside, for example, a slit shape. The entire housing 30 does not need to be formed as one component. For example, as will be described later in a modification, a portion of the housing in which the opening is formed may be detachable from another portion, or a portion of the housing may be formed integrally with a base plate 41 described later.

The user of the scanner 20 can insert the IP 10 into the insertion port 230 of the setting guide 200 through the opening 31. The IP 10 placed in the scanner 20 is set on the stage 60.

An outlet port 32 is provided in a lower portion of the housing 30, for example, in a lower portion of one side surface of the housing 30. The outlet port 32 is open outward. A recover tray 49 is disposed in the outlet port 32. For example, the recover tray 49 is formed in a box shape in which an upper side is open. The IP 10 discharged from the stage 60 is discharged to the recover tray 49. The user of the scanner 20 can pull out the recover tray 49 in the outlet port 32 to the outside and collect the read IP 10. The recover tray 49 may be detachable from the housing 30.

When the recover tray 49 is detachable, the recover tray 49 is easily cleaned. It is not essential that the configuration taking out the IP is the above configuration. A recover receiving portion that receives the IP may be exposed to the outside. The recover receiving portion may not have a tray shape, but may have a simple planar shape or a shape in which only a part of a periphery is surrounded. The recover receiving portion may not be detachable from the housing, but when the recover receiving portion is detachable, cleaning of the recover receiving portion and the like becomes easy.

A passing port conforming to the shape of the IP 10 may not be formed in at least one of the housing and the recover receiving portion.

A switch 33 that receives various instructions is provided in the housing 30. For example, the switch 33 is a power switch, a start switch that instructs start of reading.

A display device 34 may be provided in the housing 30. For example, the display device 34 is configured of a liquid crystal display panel or an organic electro-luminescence (EL) display panel. The read radiation image may be displayed on the display device 34. Various pieces of information for operation may be displayed on the display device 34. The display device 34 may display information about a reading progress status such as a remaining time from a start of reading to the end of reading. A warning, a caution, or error information for an erroneous operation or the like on the scanner 20 may be displayed on the display device 34. The display device 34 may be a touch panel having a display function and a touch detection function. In this case, at least a part of the function of the switch may be incorporated in the touch panel. The display device 34 may be omitted.

It is not essential that the image data of the radiation image generated by reading the IP 10 is displayed on the display device 34. The image data of the radiation image may be transmitted to another computer (not illustrated) that can communicate with the scanner 20 by wireless communication or wired communication. The image data of the radiation image may be recorded on a data recording medium (for example, flash memory) detachably attached to the scanner 20.

<Housing Inside Configuration>

A configuration of each portion provided inside the housing 30 will be described.

A support member 40 is provided inside the housing 30. The stage 60, the excitation light source 92, the photodetector 94, and the setting guide 200 are supported by the support member 40. The following example is an example, and for example, the configuration supporting the stage and the setting guide is not limited to the following configuration. The configuration related to the support member does not limit the present disclosure, and the present disclosure can be applied to various configurations that guide the IP 10 to the stage using gravity.

<Support Member>

As illustrated in FIGS. 1 to 3, the support member 40 includes a base plate 41, an intermediate support plate 42, and a box-shaped portion 44.

The base plate 41 is a plate member disposed along a horizontal direction (a direction perpendicular to a direction of gravity) at a lower portion in the internal space of the housing 30. Here, the base plate 41 is formed in an elongated rectangular plate shape. The base plate 41 can close the downward opening of the housing 30.

The intermediate support plate 42 is supported on the base plate 41 in an erected state. The intermediate support plate 42 is a plate including an inclined surface (second IP guide surface) 42a inclined with respect to a gravity direction (see FIG. 3). The inclined surface 42a is a surface facing obliquely upward. In the first embodiment, the intermediate support plate 42 is formed in a shape in which one upper corner of the rectangle is obliquely cut. The box-shaped portion 44 is supported on the inclined surface 42a, whereby the box-shaped portion 44 is supported in an oblique posture.

In the first embodiment, a circuit unit 43 is supported by the intermediate support plate 42. For example, the circuit unit 43 is a unit in which various electric components are mounted on a circuit board. For example, such a circuit unit may be a control unit that executes various controls of the scanner 20, or may be a power supply circuit that supplies power to each unit of the scanner 20. The circuit unit 43 may be supported by another portion other than the intermediate support plate 42, for example, the base plate 41, the housing 30, or the box-shaped portion 44.

The box-shaped portion 44 includes a pair of longitudinal-direction side plates 45, a pair of lateral-direction side plates 46, and a back plate 47. The back plate 47 has a rectangular plate shape elongated in one direction. Each of the pair of longitudinal-direction side plates 45 is formed in a rectangular plate shape corresponding to a length of the long side of the back plate 47, and the pair of longitudinal-direction side plates 45 is supported in the erected state on the pair of long sides of the back plate 47. Each of the lateral-direction side plates 46 is formed in a rectangular plate shape corresponding to the length of the short side of the back plate 47. A pair of lateral-direction side plates 46 are supported in the erected state on the pair of short sides of the back plate 47. Thus, the box-shaped portion 44 is formed in a box shape, in which the back plate 47 is a bottom and one surface side of the bottom is surrounded by the pair of longitudinal-direction side plates 45 and the pair of lateral-direction side plates 46. Hereinafter, the upper one of the pair of lateral-direction side plates 46 may be distinguished as a lateral-direction side plate 46U, and the lower one may be distinguished as a lateral-direction side plate 46L. The box-shaped portion 44 is open on the opposite side of the back plate 47. The pair of longitudinal-direction side plates 45 and the pair of lateral-direction side plates 46 are fixed to the back plate 47 by, for example, screwing or welding.

The back plate 47 is supported by the inclined surface 42a of the intermediate support plate 42 along the inclined surface. The back plate 47 is supported in an oblique posture along the inclination of the inclined surface 42a. The back plate 47 is fixed to the intermediate support plate 42 by, for example, screwing or welding.

The pair of longitudinal-direction side plates 45 and the pair of lateral-direction side plates 46 are erected on the side opposite to the intermediate support plate 42 with respect to the back plate 47. The box-shaped portion 44 is open obliquely upward on the side opposite to the intermediate support plate 42.

The pair of longitudinal-direction side plates 45 extends along the extending direction of the inclined surface 42a. For this reason, an edge of the pair of longitudinal-direction side plates 45 on the side opposite to the back plate 47 is also inclined with respect to the gravity direction along the extending direction of the inclined surface 42a. A pair of support rods 48 is supported on the edges of the pair of longitudinal-direction side plates 45 opposite to the back plate 47 in a posture inclined with respect to the gravity direction. For example, the support rod 48 is supported by being screwed or welded to at least one of the longitudinal-direction side plate 45 and the lateral-direction side plate 46.

In the first embodiment, the support rod 48 is formed in a square rod shape. The support rod 48 is longer than the longitudinal-direction side plate 45. One end of the support rod 48 reaches the upper lateral-direction side plate 46U along the edge portion of the longitudinal-direction side plate 45. The other end of the support rod 48 further extends obliquely downward beyond the lower lateral-direction side plate 46L along the edge portion of the longitudinal-direction side plate 45. The other end of the support rod 48 is a lower end and is positioned above the base plate 41.

The excitation light source 92 and the photodetector 94 are attached to an outward surface of the pair of support rods 48 opposite to the back plate 47. The excitation light source 92 and the photodetector 94 are located between the pair of lateral-direction side plates 46 and are closer to the lower lateral-direction side plate 46L. The excitation light source 92 emits excitation light toward the side of the box-shaped portion 44, and the photodetector 94 detects light from the side of the box-shaped portion 44. Attachment of the excitation light source 92 and the photodetector 94 to the support rod 48 is performed by, for example, screwing.

The stage 60 is movably supported inside the excitation light source 92 and the photodetector 94 between the pair of longitudinal-direction side plates 45. In the following description, for convenience, the side of the stage 60 on which the excitation light source 92 and the photodetector 94 are provided is sometimes referred to as a front side, and the opposite side is sometimes referred to as a rear side. In the following description, a relative movement direction of the stage 60 with respect to the excitation light source 92 and the photodetector 94 may be referred to as a main scanning direction A1. When the IP 10 held by the stage 60 passes through the space between the excitation light source 92 and the photodetector 94, the IP 10 is radiated with the excitation light from the excitation light source 92, and the emission light of the IP 10 due to the excitation light is detected by the photodetector 94.

The setting guide 200 is attached to a portion of the pair of support rods 48 extending downward from the lower lateral-direction side plate 46L. The setting guide 200 is attached to the support rod 48 by, for example, screwing.

The stage 60 can move to a position extending downward from the lower lateral-direction side plate 46L in the extending direction of the support rod 48. The user can set the IP 10 on the stage 60 through the setting guide 200 while the stage 60 is moved to the position extending downward from the lateral-direction side plate 46L.

In addition, the recover tray 49 is positioned on an obliquely downward extension of the pair of support rods 48. The IP 10 discharged from the stage 60 falls into the recover tray 49 and is collected while the stage 60 moves to the position extending downward from the lateral-direction side plate 46L. The recover tray 49 does not need to be movably disposed with respect to the housing 30. For example, the recover tray located on the extension of the support rod may be open to the outside of the housing from the side opposite to the intermediate support plate, and the IP in the recover tray may be taken out to the outside of the housing through the opening.

In the first embodiment, the pair of longitudinal-direction side plates 45 is supported at a fixed position in the housing 30 in the form of the box-shaped portion 44. The configuration in which the longitudinal-direction side plate 45 is supported at the fixed position in the box-shaped portion 44 is not limited to this example. For example, the longitudinal-direction side plate 45 may be fixed to a side surface or the like that is a part of the housing 30.

The box-shaped portion 44 is not limited to the configuration in which a plurality of plate members are fixed by screwing, welding, or the like. The entire box-shaped portion may be an integral member formed by press working, die molding, or the like. In this case, it is possible to eliminate screwing and welding in order to manufacture the box-shaped portion.

<Excitation Light Source and Photodetector>

The excitation light source 92 irradiates the IP 10 held by the stage 60 with the excitation light. The excitation light is light exciting the radiation image forming layer 11, and for example, is laser light of a specific wavelength exciting the radiation image forming layer 11. When the radiation image forming layer 11 is irradiated with the excitation light, the radiation image forming layer 11 emits light according to a distribution of the energy accumulated in the radiation image forming layer 11.

The excitation light source 92 may include a laser light source that emits the laser light as the excitation light and a micro electro mechanical systems (MEMS) mirror. For example, the laser light source may be reflected by the MEMS mirror such that an irradiation destination of the laser light from the laser light source moves along a sub-scanning direction A2 intersecting (orthogonal to) the main scanning direction A1 with respect to the front surface 10a of the radiation image forming layer 11. A galvanometer mirror, a polygon mirror, or the like can be used as the configuration of the mirror instead of the MEMS mirror. Sometimes the configuration of a lens system is additionally required depending on the configuration of the mirror, but can be used in the scanner by an appropriate combination.

The photodetector 94 is a sensor that detects the light emitted from the IP 10 by the excitation light and outputs a signal corresponding to the intensity. The image data of the radiation image is generated based on the signal from the photodetector 94.

The photodetector 94 may have a configuration in which elements detecting the light are arranged in a line. For example, the photodetector 94 may be arranged in a posture in which the array direction of the elements is parallel to the sub-scanning direction A2. The element that detects the light may be a silicon photomultiplier, a photomultiplier, a photodiode, or the like.

In one embodiment, the excitation light source 92 and the photodetector 94 are integrated as a reading unit 90. For example, the excitation light source 92 and the photodetector 94 are integrated while being accommodated in a module case 91. A reading slit 90S elongated along the sub-scanning direction A2 is formed in a portion of the module case 91 facing the side of the support member 40 (see FIG. 3). The excitation light is emitted toward the IP 10 through the reading slit 90S. The emission light of the IP 10 passes through the reading slit 90S and is detected by the photodetector 94.

During the movement of the stage 60 along the main scanning direction A1, the laser light from the excitation light source 92 enters the front surface 10a of the radiation image forming layer 11 of the IP 10 held by the stage 60, and the irradiation destination moves along the sub-scanning direction A2. Thus, the front surface 10a of the radiation image forming layer 11 sequentially generates the emission light along the line along the sub-scanning direction A2.

The photodetector 94 is provided at a position where the emission light of the radiation image forming layer 11 generated by the laser light from the excitation light source 92 can be detected. For example, the excitation light source 92 is disposed to irradiate the IP 10 with the laser light from an oblique direction, and the photodetector 94 is disposed in front of a position irradiated with the laser light on the IP 10. When the surface of the radiation image forming layer 11 sequentially generates the emission light along the line along the sub-scanning direction A2, the emission light is detected by the photodetector 94.

During the movement of the stage 60, scanning of the excitation light source 92 in the sub-scanning direction A2 and scanning by the photodetector 94 are repeatedly performed, so that a radiation image of a wide surface of the IP 10, for example, the entire surface of the IP 10, is read by the photodetector 94.

It is not essential to perform the reading during the movement of the stage 60. For example, the excitation light source 92 and the photodetector 94 may move while the stage 60 is stopped. Alternatively, the stage 60 and both the excitation light source 92 and the photodetector 94 may move.

<Stage and Stage Movement Configuration>

Figure 4:
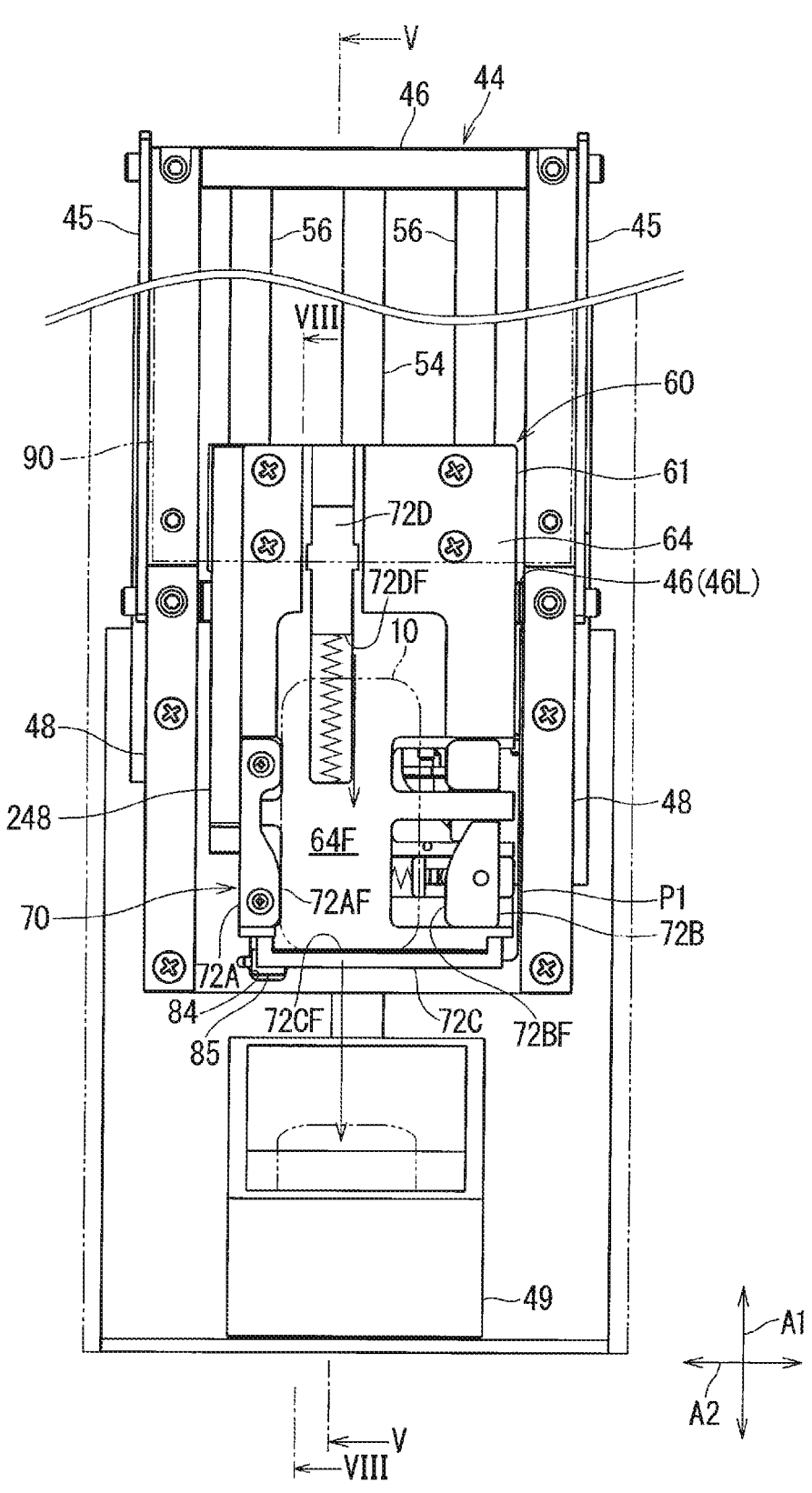
FIG. 4 is a front view illustrating an internal structure of the scanner.

FIG. 4 is a front view illustrating the internal structure of the scanner 20 as viewed from the outside orthogonal to the supporting surface 64F of the stage 60. In FIG. 4, the reading unit 90 and the setting guide 200 are omitted. FIG. 5 is a sectional view taken along a line V-V in FIG. 4. In FIG. 5, the setting guide 200 is not omitted, and the reading unit 90 is indicated by a two-line chain line.

As illustrated in FIGS. 1 to 5, the stage 60 is configured to hold the IP 10. For example, the stage 60 includes a plate portion that expands larger than the IP 10. The IP 10 is held at the fixed position and in a fixed posture with respect to the stage 60 while being in contact with the supporting surface 64F on one surface side of the stage 60. A configuration in which the stage 60 holds the IP 10 will be described later in more detail.

The stage 60 moves along the main scanning direction A1 while holding the IP 10. A configuration movably supporting the stage 60 will be described.

The stage 60 can move along the main scanning direction A1 between the edges of the pair of longitudinal-direction side plates 45 opposite to the back plate 47. A protruding dimension of the lower lateral-direction side plate 46L with respect to the back plate 47 is smaller than a protruding dimension of the longitudinal-direction side plate 45 with respect to the back plate 47. For this reason, the stage 60 can move downward along the main scanning direction A1 from between the pair of longitudinal-direction side plates 45 over the lower lateral-direction side plate 46L. That is, the stage 60 can reciprocate along the main scanning direction A1 between the position (positions P2, P4 indicated by two-dot chain lines in FIG. 2) between the pair of longitudinal-direction side plates 45 and the position P1 (see FIG. 2) protruding downward between the pair of longitudinal-direction side plates 45.

The stage 60 is configured to be movable and driven by a stage moving mechanism 50. The stage moving mechanism 50 includes a movement driving portion 52 and a pair of guide rods (stage guide) 56.

The movement driving portion 52 applies driving force along the main scanning direction A1 to the stage 60. In the first embodiment, the movement driving portion 52 includes a motor 53 and a screw shaft portion 54. The screw shaft portion 54 is a rod member in which a screw groove is formed around the screw shaft portion. The screw shaft portion 54 is rotatably supported by the pair of lateral-direction side plates 46 to be bridged between the pair of lateral-direction side plates 46. The motor 53 is unrotatably fixed to the box-shaped portion 44. For example, the motor 53 is unrotatably fixed to the outside of the lower lateral-direction side plate 46L through a bracket 53B or the like. A shaft 53a of the motor 53 is fixed to the screw shaft portion 54 to not rotate relative to the screw shaft portion 54, and the screw shaft portion 54 is rotationally driven in a forward rotation direction or a reverse rotation direction according to the rotation in the forward rotation direction or the reverse rotation direction of the motor 53. The rotational movement of the shaft 53a of the motor 53 may be transmitted to the screw shaft portion 54 through a transmission device such as a gear or a pulley.

The stage 60 includes a through-hole 62h1 including a screw groove (see FIG. 2). The screw shaft portion 54 is screwed into the through-hole 62h1. The rotation of the screw shaft portion 54 drives the stage 60 to which the screw shaft portion 54 is screwed such that the stage 60 moves along the main scanning direction A1.

The guide rod 56 is an elongated rod member, and is fixed to the pair of lateral-direction side plates 46 to be bridged between the pair of lateral-direction side plates 46. The guide rod 56 is inserted through a guide hole 62h2 formed in the stage 60 (see FIG. 2). Accordingly, the guide rod 56 can play a role of preventing the rotation of the stage 60 around the screw shaft portion 54. In this case, a plurality of (in the first embodiment, two) guide rods 56 are provided. However, one guide rod may be provided.

The movement direction by the movement driving portion 52 is not limited to the above example, but may be a horizontal direction or an oblique direction. The movement driving portion 52 only needs to be an actuator that moves the stage 60, and may be a linear motor or the like or a mechanism that moves by a belt in addition to the above configuration. Instead of the movement of the stage, the reading unit 90 may be moved to read the IP on the stage. When the reading unit is a sensor capable of reading plane information of the IP, both the stage and the reading unit may not move.

The stage 60 is reciprocated between a setting position P1 and a reading position P2 by the stage moving mechanism 50.

The setting position P1 is a position where the IP 10 can be set with respect to the stage 60. In the first embodiment, the setting position P1 is set at a position protruding to the outside (lower side) of the lower lateral-direction side plate 46L. At the setting position P1, the portion near the upper end of the stage 60 is disposed on the lateral-direction side plate 46L, and the intermediate portion and the lower end in the longitudinal direction of the stage 60 extend downward from the lower lateral-direction side plate 46L. At the setting position P1, an arrangement region of the IP 10 set on the stage 60 (a maximum arrangement region when the IPs 10 of a plurality of sizes are assumed) is disposed outside the lower lateral-direction side plate 46L.

In this state, the supporting surface 64F of the stage 60 is inclined with respect to the direction of gravity. In this case, the supporting surface 64F is inclined along the same inclination direction as the extending direction of the longitudinal-direction side plate 45. That is, the supporting surface 64F is inclined to face obliquely upward. In the first embodiment, the supporting surface 64F is an inclined surface inclined to the opposite side with respect to an IP guide surface 216 described later. The supporting surface 64F as the inclined surface will be further described later in relation to the IP guide surface.

The stage 60 located at the setting position P1 can receive the IP 10 guided by the setting guide 200. More specifically, the setting position P1 is provided below the setting guide 200 (see FIG. 5). When the IP 10 is inserted into the insertion port 230 of the setting guide 200 from the outside of the scanner 20, the IP 10 moves downward in the gravity direction by its own weight while being guided by the setting guide 200. When the lower edge portion of the IP 10 reaches the supporting surface 64F, the IP 10 is inclined toward the supporting surface 64F while the lower edge portion of the IP 10 slides down obliquely in accordance with the inclination of the supporting surface 64F, and the back surface 10b of the IP 10 can be brought into surface contact with the supporting surface 64F. In this state, the IP 10 is positioned and held by a positioning mechanism (described later) provided on the stage 60. In one embodiment, as described above, the gravity is used when the IP 10 is guided to the normal posture.

The configuration in which the setting guide 200 guides the IP 10 will be described later in more detail.

The setting position P1 is not necessarily set to the above position, but for example, may be set between the pair of longitudinal-direction side plates 45 according to the positional relationship with the setting guide 200.

The reading position P2 is a position where the excitation light source 92 and the photodetector 94 read the radiation image, namely, a position where the photodetector 94 reads the radiation image of the IP 10 according to the excitation light from the excitation light source 92. In the first embodiment, the reading position P2 is set at the position between the pair of longitudinal-direction side plates 45. More specifically, the reading position P2 is set between the pair of longitudinal-direction side plates 45 and at a lower position.

That is, the reading unit 90 including the excitation light source 92 and the photodetector 94 is fixed to the pair of support rods 48 by screwing or the like between the outward edge portions of the pair of longitudinal-direction side plates 45. The reading unit 90 is located between the pair of longitudinal-direction side plates 45 and closer to the setting position P1. The reading slit 90S is formed on the surface of the reading unit 90 facing the inside of the box-shaped portion 44. The excitation light from the excitation light source 92 in the reading unit 90 is emitted to the IP 10 on the stage 60 through the reading slit 90S. In addition, the emission light from the IP 10 excited by the excitation light is incident on the photodetector 94 through the reading slit 90S.

When being set on the stage 60 at the setting position P1, the IP 10 moves toward the inside of the box-shaped portion 44 along the main scanning direction A1. When the IP 10 set on the stage 60 reaches the position facing the reading slit 90S, the reading unit 90 starts the reading of the radiation image of the IP 10. As the stage 60 moves, the radiation image of the IP 10 is sequentially read by the reading unit 90. When the IP 10 passes through the reading slit 90S, the reading by the reading unit 90 ends. When the radiation image is read during the movement of the stage 60 as in the first embodiment, the reading position P2 may be regarded as the position where the IP 10 (the widest IP 10 in the case where the IPs 10 of a plurality of sizes are assumed) on the stage 60 reaches the reading slit 90S to start the reading.

Unlike the above example, the case where the reading unit 90 moves along the main scanning direction A1 with respect to the IP 10 stationary at the fixed position to read the radiation image or the case where a two-dimensional sensor reads the radiation image with respect to the IP 10 stationary at the fixed position is also assumed. In this case, the position where the IP 10 is held at the fixed position is the reading position P2.

In first embodiment, the stage moving mechanism 50 causes the stage 60 to also move to an eject position P3 (see FIG. 5). The eject position P3 is a position where the IP 10 set on the stage 60 is ejected. The eject position P3 is set at the position farther from the reading position P2 than the setting position P1 (see the stage 60 indicated by a two-dot chain line in FIG. 5). The present disclosure is not limited to this example, but the IP 10 of the stage 60 may be ejected by a separate mechanism at a position different from the eject position P3, for example, at the setting position P1.

As described above, the recover tray 49 is provided below the eject position P3. The upper opening of the recover tray 49 is open on the lower extension of the stage 60. The IP 10 slides down on the stage 60 at the eject position P3 and is discharged into the recover tray 49 through the upper opening of the recover tray 49.

In the first embodiment, the stage moving mechanism 50 causes the stage 60 to also move to the inner side position P4 (see FIG. 2). The inner side position P4 is located on the opposite side of the reading position P2 from the setting position P1. That is, the stage 60 can move from the setting position P1 to the inner side position P4 through the reading position P2. At the inner side position P4, the IP 10 on the stage 60 may be exposed without being covered by the reading unit 90 or covered by another member.

The operation of the stage moving mechanism 50 is controlled by a controller 100 (see FIG. 3). For example, the controller 100 includes a computer including at least one processor and a storage. The processor is a central processing unit (CPU) or the like, and includes an electric circuit. The processor executes a reading program to implement various functions for the reading. The controller 100 controls the rotation direction and the rotation amount of the motor 53 to control the movement of the stage 60 along the main scanning direction A1. The controller 100 is assumed to be a circuit implemented by the circuit unit 43 (see FIG. 3).

The controller 100 may control the excitation light source 92 and the photodetector 94 by the reading unit 90. Various types of signal processing for generating the radiation image based on the signal detected by the photodetector 94, image processing, display processing by the display device 34, and the like may be performed by the controller 100.

The configuration in which the stage 60 is moved is not limited to the above example. The moving mechanism may move the reading unit 90 in the gravity direction, the horizontal direction, or the oblique direction. Furthermore, the stage 60 may be supported at the fixed position, and the reading unit 90 may move.

<Overall Configuration of Stage>

The overall configuration of the stage 60 will be described. As illustrated in FIGS. 1 to 5, the stage 60 includes a stage body 61 and a positioning mechanism 70.

The stage body 61 includes the supporting surface 64F that can be brought into surface contact with the back surface 10b of the IP 10. In one embodiment, the stage body 61 includes a movable support 62 and a plate portion 64.

The movable support 62 is formed in a rectangular parallelepiped shape. The through-hole 62h1 is made in the movable support 62 (see FIG. 2). As described above, the screw shaft portion 54 rotatable in both forward and reverse directions by the motor 53 is screwed into the through-hole 62h1. The stage 60 moves to one side along the screw shaft portion 54 when the screw shaft portion 54 rotates in the forward rotation direction, and the stage 60 can move to the other side along the screw shaft portion 54 when the screw shaft portion 54 rotates in the reverse rotation direction. For example, such the structure is a structure called a ball screw.

The guide hole 62h2 parallel to the through-hole 62h1 is made in the movable support 62 (see FIG. 2). Thus, the movable support 62 is moved and driven in both directions along the main scanning direction A1 according to the rotation in the forward rotation direction or the reverse rotation direction of the screw shaft portion 54 screwed into the through-hole 62h1 under the guide of the guide rod 56 inserted into the guide hole 62h2.

The plate portion 64 is formed in a shape that is larger than the IP 10 and spreads in a plate shape, in this case, a rectangular plate shape. The plate portion 64 is not necessarily formed in the rectangular plate shape, but may be formed in another shape such as an elliptical shape.

The supporting surface 64F is provided on the surface on one side of the plate portion 64. The supporting surface 64F may be wider than the IP 10. When multiple sizes are contemplated for the IP 10, the supporting surface 64F may be wider than the largest IP 10.

More specifically, the plate portion 64 is formed in a rectangular shape elongated along one direction (in this case, the main scanning direction A1). Of the surface on the other side of the plate portion 64 (the surface on the side opposite to the supporting surface 64F), a portion on one side in the longitudinal direction of the plate portion 64 is fixed to the movable support 62. For example, the fixing is performed by screwing. The plate portion 64 is supported in a cantilever manner by the movable support 62 to extend from the movable support 62 toward the side of the setting position P1 along the main scanning direction A1. In the surface on one side of the plate portion 64, a part of a portion extending downward from the movable support 62 along the main scanning direction A1 is recessed more than other portions. The bottom surface of the recessed portion is the supporting surface 64F that can be brought into surface contact with the back surface of the IP 10.

While the stage 60 is supported by the support member 40, the plate portion 64 and the supporting surface 64F are inclined with respect to the gravity direction (downward direction), and the supporting surface 64F is directed obliquely upward. In the first embodiment, the inclination angles of the plate portion 64 and the supporting surface 64F coincide with the inclination angle in the extending direction of the longitudinal-direction side plate 45 and the inclination angle of the pair of support rods 48. The plate portion 64 and the supporting surface 64F move along the main scanning direction A1 under the guide of the guide rod 56 while maintaining a constant inclination angle. When the movable support 62 moves toward the lower lateral-direction side plate 46L, a portion of the plate portion 64 extending from the movable support 62 passes over the lower lateral-direction side plate 46L and extends obliquely downward. In this state, because the supporting surface 64F is inclined to face obliquely upward, the IP 10 supplied through the setting guide 200 can be received on the supporting surface 64F.

In the first embodiment, a partial protrusion region 64P (see FIGS. 6 and 7) is formed in a region of the plate portion 64 close to the movable support 62. The protrusion region 64P is formed in a region surrounding the upper side and both sides of the supporting surface 64F. There is a step between the protrusion region 64P and the supporting surface 64F. The existence of the protrusion region 64P allows the IP 10 to be more reliably supported on the supporting surface 64F. The existence of the protrusion region 64P is not essential.

The positioning mechanism 70 includes positioning surfaces 72AF, 72BF, 72CF, 72DF that come into contact with the edge portion of the IP 10 supported on the supporting surface 64F and position the edge portion from the outside in the extending direction of the supporting surface 64F. In the first embodiment, the positioning surfaces 72AF, 72BF, 72CF, 72DF are inclined to form an acute angle with respect to the supporting surface 64F, and press the edge portion of the IP 10 against the supporting surface 64F. It is not essential that the positioning surfaces 72AF, 72BF, 72CF, 72DF have a configuration in which the edge portion of the IP 10 is pressed against the supporting surface 64F.

The stage 60 does not need to have the positioning mechanism 70, and for example, when the stage 60 is in a horizontal posture orthogonal to the gravity direction, the IP 10 may be placed on the stage 60 without being positioned at the edge portion.

In the configuration in which the stage 60 includes the positioning mechanism 70, the positioning mechanism 70 may have at least one of the positioning surfaces 72AF, 72BF, 72CF, 72DF. In order that the positioning mechanism 70 positions the IP 10 in at least two directions, the positioning mechanism 70 may have at least two positioning surfaces 72AF, 72BF, 72CF, 72DF facing different directions (for example, directions orthogonal to each other). For example, the positioning mechanism may have an upward positioning surface that supports the IP 10 from below, and a rightward or leftward positioning surface that presses the IP 10 in the left-right direction from one side. In one embodiment, the positioning mechanism 70 include a horizontal positioning mechanism and a vertical positioning mechanism. For this reason, the IP 10 is positioned at the fixed position in the horizontal direction and the vertical direction.

The IP 10 moves to the reading position P2 while being held in the normal posture by the positioning mechanism 70. At the reading position P2, the radiation image of the IP 10 held in the normal posture on the stage 60 is read by the reading unit 90. The normal posture is a posture of the IP 10 predetermined with respect to the stage 60, and is a predetermined posture suitable for the reading by the reading unit 90. In the first embodiment, the positioning surfaces 72AF, 72CF are disposed at the fixed positions on the supporting surface 64F of the stage 60 at the setting or reading time. The normal posture is a state in which the edge portion on one side of the IP 10 is in contact with the positioning surface 72AF while the edge portion on the lower side of the IP 10 is in contact with the positioning surface 72CF.

In the first embodiment, the stage 60 supports the longitudinal direction of the IP 10 in a posture in which the longitudinal direction of the IP 10 is inclined with respect to the horizontal direction. Specifically, the longitudinal directions of the plate portion 64 and the supporting surface 64F on one surface side of the plate portion 64 are inclined with respect to the horizontal direction, and the lateral directions are along the horizontal direction. For this reason, when the IP 10 is supported on the stage 60 in a posture in which the longitudinal direction of the IP 10 is along the longitudinal directions of the plate portion 64 and the supporting surface 64F, the longitudinal direction of the IP 10 is inclined with respect to the horizontal direction.

In the first embodiment, a minimum interval between positioning holders 72A, 72B in the sub-scanning direction A2 (horizontal direction) is smaller than a minimum interval between positioning holders 72C, 72D in the main scanning direction A1. The maximum interval between the positioning holders 72A, 72B in the sub-scanning direction A2 (horizontal direction) is smaller than the maximum interval between the positioning holders 72C, 72D in the main scanning direction A1. For this reason, the stage 60 has a configuration in which the longitudinal direction of the IP 10 is suitably supported in a posture along the longitudinal directions of the plate portion 64 and the supporting surface 64F.

Regardless of the first embodiment, the stage may support the IP in a posture in which the lateral direction of the IP is inclined with respect to the horizontal direction. For example, the longitudinal directions of the plate portion and the supporting surface of the stage may be along the horizontal direction, and the lateral direction may be inclined with respect to the horizontal direction.

<Positioning Mechanism>

Figure 6:
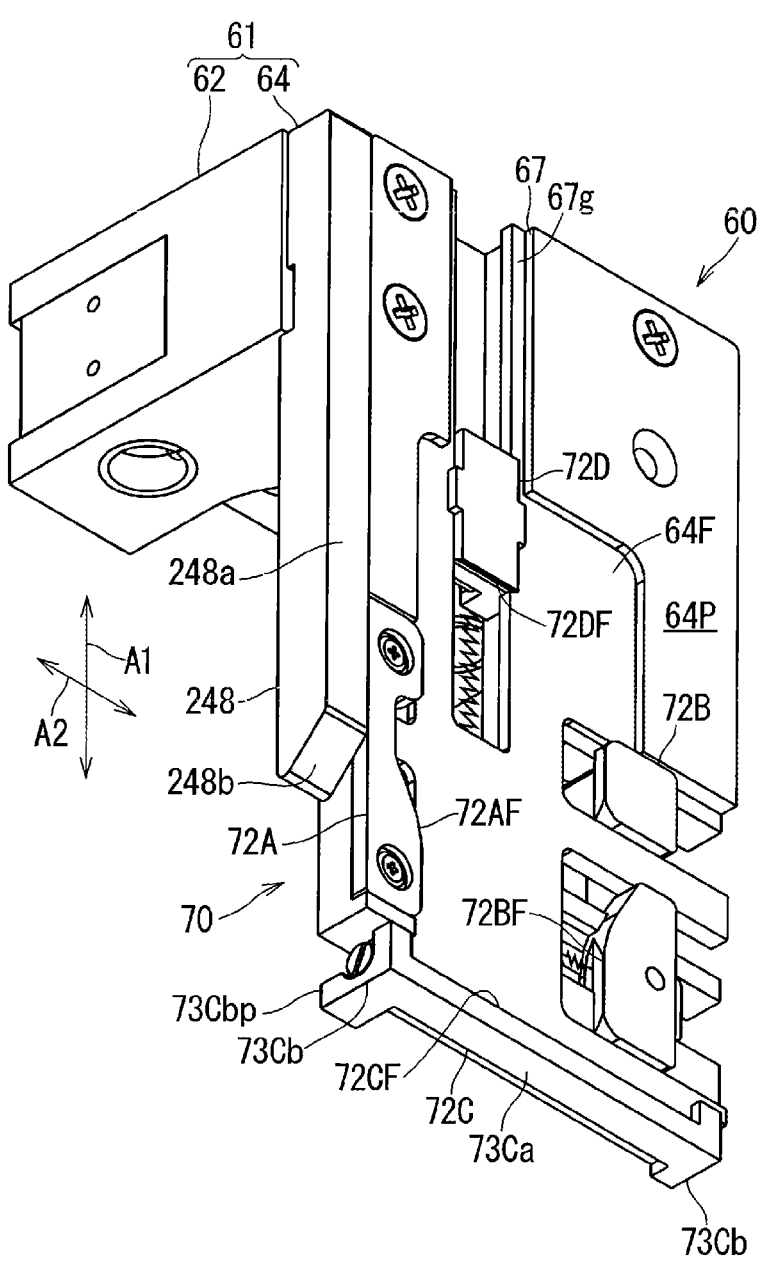
FIG. 6 is a perspective view illustrating a stage.
Figure 7:
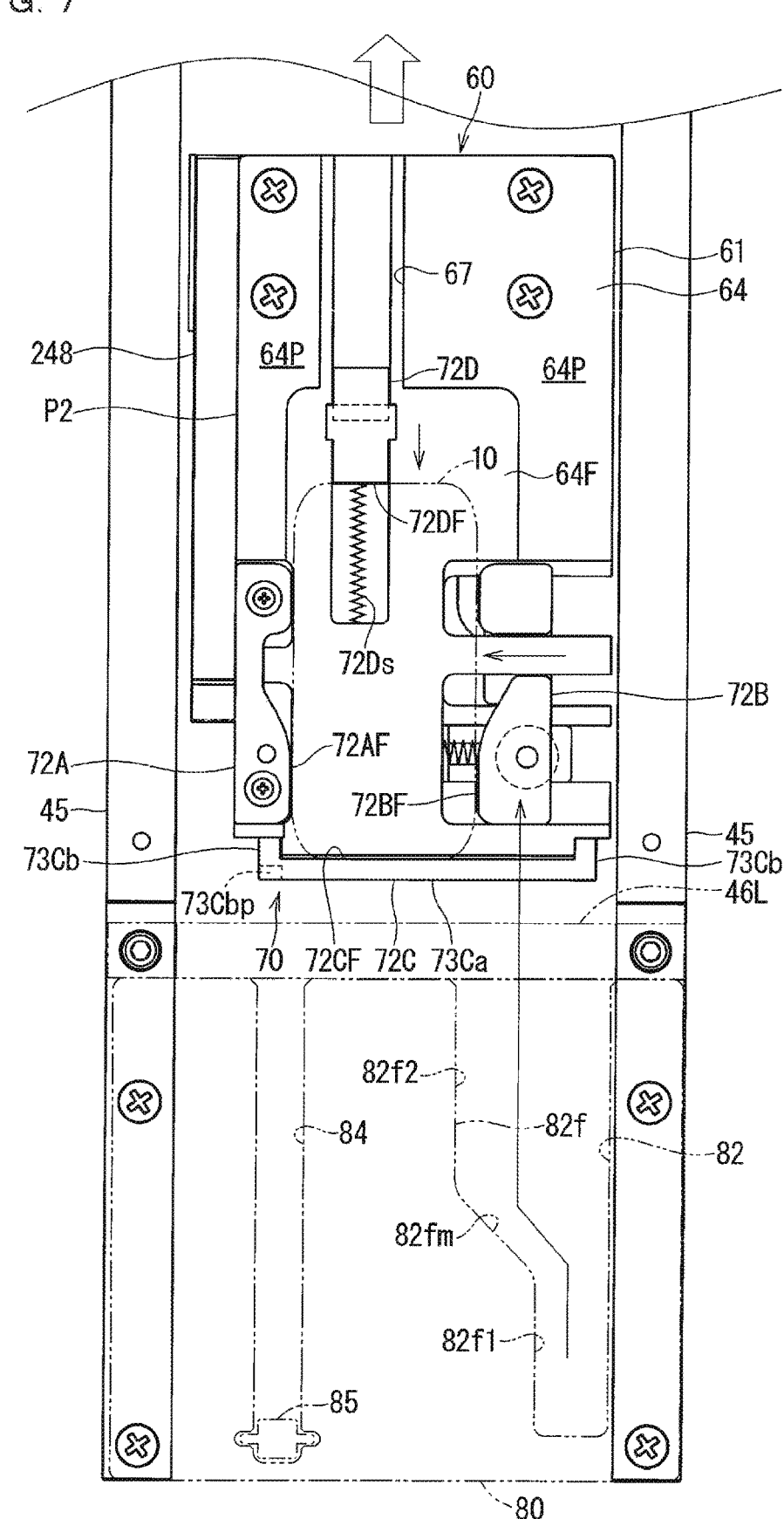
FIG. 7 is a front view illustrating the stage at a reading position.
Figure 8:
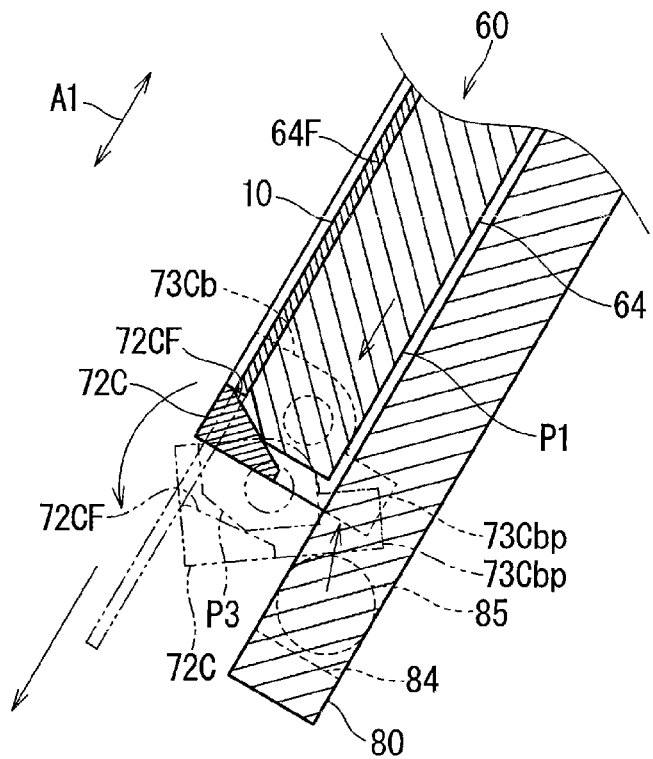
FIG. 8 is a partially sectional view taken along a line VIII-VIII in FIG. 4.

FIG. 6 is a perspective view illustrating the stage 60. FIG. 7 is a front view illustrating the stage 60 at the reading position P2, and FIG. 8 is a partially sectional view taken along a line XIII-XIII in FIG. 4.

The positioning mechanism 70 includes four positioning holders 72A, 72B, 72C, 72D. The positioning holders 72A, 72B position the IP 10 in the sub-scanning direction A2 (in the first embodiment, in the horizontal direction,), and the positioning holders 72C, 72D position the IP 10 in the main scanning direction A1 (in the first embodiment, the vertical direction). When the IP 10 is located at the setting position P1, the right and left positioning holders 72A, 72B are open, and the upper and lower positioning holders 72C, 72D are also open (see FIG. 4). In this state, the IP 10 can be set on the stage 60. When the IP 10 is located at the reading position P2, the right and left positioning holders 72A, 72B approach each other, and the upper and lower positioning holders 72C, 72D also approach each other. In this state, the IP 10 is held on the stage 60 while being positioned in both the main scanning direction A1 and the sub-scanning direction A2.

The configuration in which the left and right positioning holders 72A, 72B and the upper and lower positioning holders 72C, 72D are opened and closed is not particularly limited.

For example, at least one of the left and right positioning holders 72A, 72B may be biased in the closing direction by a biasing member such as a spring. In this case, when the stage 60 moves to the setting position P1, at least one of the left and right positioning holders 72A, 72B may be pressed against a fixing portion such as a cam surface and opened against the biasing force of the biasing member. In addition, when the stage 60 moves to the reading position P2, the position restriction by the cam surface or the like may be released, and at least one of the left and right positioning holders 72A, 72B may move toward a closed position by the biasing force of the biasing member.

Furthermore, for example, at least one of the left and right positioning holders 72A, 72B may be driven by a driving unit (for example, a motor or a solenoid actuator) for opening and closing.

The upper and lower positioning holders 72C, 72D may also be driven to open and close by the same configuration as that for driving the left and right positioning holders 72A, 72B.

Both the left and right positioning holders 72A, 72B may be fixed at the fixed positions with respect to the stage 60. Both or one of the left and right positioning holders 72A, 72B may be omitted.

In addition, both the upper and lower positioning holders 72C, 72D may be fixed at the fixed positions with respect to the stage 60. Both or one of the upper and lower positioning holders 72C, 72D may be omitted.

However, assuming that the stage 60 is in an oblique posture, the lower positioning holder 72C plays a role of receiving the IP 10 sliding down on the supporting surface 64F from below.

The positioning holder 72C will be described. The positioning holder 72C is an elongated portion protruding from one side portion of the plate portion 64 in the main scanning direction A1, in this case, a lower side portion. The positioning holder 72C extends along the sub-scanning direction A2 along the lower boundary of the boundary surrounding the supporting surface 64F. The positioning holder 72C protrudes from the supporting surface 64F. The length of the positioning holder 72C may be longer than the left-right dimension (the maximum left-right dimension when the plurality of sizes are assumed) of the IP 10 supported on the supporting surface 64F.

The surface of the positioning holder 72C facing the inside (upper side) is formed on the positioning surface 72CF. The positioning surface 72CF may be formed on a guide surface (in this case, a plane) in which an angle with respect to the supporting surface 64F is less than 90°, or may be formed on a plane perpendicular to the supporting surface 64F. Because the positioning surface 72CF is located below the supporting surface 64F inclined with respect to the direction of gravity, the positioning surface 72CF is an example of the surface that receives the lower edge portion of the IP 10 moving downward along the supporting surface 64F.

In one embodiment, the positioning holder 72C is formed separately from the plate portion 64. The posture of the positioning holder 72C is configured to be changeable between a contact position and a retreat position (see FIG. 8). The contact position is a position where the positioning surface 72CF is opposite to the edge portion of the IP 10 on the supporting surface 64F, and the retreat position is a position where the positioning surface 72CF is retreated from the edge portion of the IP 10 on the supporting surface 64F.

The operation of the positioning holder 72C will be described. A lower end side portion of the plate portion 64 is formed to be narrower than other portions. The positioning holder 72C includes an elongated positioning body portion 73Ca and a pair of rotation support portions 73Cb. The positioning body portion 73Ca is set to have a length that can extend over the entire lower end side portion of the plate portion 64. One of the surfaces surrounding the periphery of the positioning body portion 73Ca is formed on the positioning surface 72CF. The pair of rotation support portions 73Cb extends from both ends of the positioning body portion 73Ca. The pair of rotation support portions 73Cb is disposed outside the lower end side portion of the plate portion 64 on both sides. The pair of rotation support portions 73Cb is rotatably supported with respect to both sides of the lower end side portion of the plate portion 64 by a support shaft portion configured by a screw, a pin, or the like.

As described above, the positioning surface 72CF is located to intersect on the downward extension of the supporting surface 64F while the positioning holder 72C is located at the contact position. For this reason, the lower edge portion of the IP 10 sliding down on the supporting surface 64F can come into contact with the positioning surface 72CF (see the positioning holder 72C indicated by a solid line in FIG. 8).

When the position of the positioning surface 72CF is changed to the retreat position, the positioning surface 72CF retreats from the supporting surface 64F (see the positioning holder 72C indicated by a two-dot chain line in FIG. 8). That is, the positioning surface 72CF at the retreat position is not positioned at the position receiving the lower edge portion of the IP 10 moved downward along the supporting surface 64F. In the first embodiment, the positioning surface 72CF retreats toward the back side of the supporting surface 64F. The positioning surface 72CF may retreat to the front side of the supporting surface 64F. When the positioning surface 72CF moves to the retreat position, the IP 10 can slide down on the supporting surface 64F.

In the first embodiment, a protruding piece 73Cbp protruding to the side opposite to the supporting surface 64F is provided in a protruding manner on one of the pair of rotation support portions 73Cb. When the protruding piece 73Cbp is pushed by the movement of the stage 60, the positioning surface 72CF is positionally changed from the contact position to the retreat position. The positioning holder 72C may be biased from the retreat position to the retreat position by an own weight of the positioning holder 72C or a spring such as a torsion coil spring.

A configuration in which the position of the positioning holder 72C is changed will be described.

In first embodiment, the stage 60 is movable to the eject position P3 that is further away from the setting position P1 (to the side opposite to the reading position P2) (see FIGS. 5 and 8).

A cam plate 80 is supported by a portion of the pair of support rods 48 protruding from the box-shaped portion 44. The cam plate 80 is a plate member located between the pair of support rods 48 outside the lower lateral-direction side plate 46L. The cam plate 80 is located on the side opposite to the supporting surface 64F with respect to the stage body 61 at the reading position P2.

A groove 84 is formed in the cam plate 80 (see FIGS. 4 and 8). The groove 84 is formed to extend along the main scanning direction A1 at a position where the protruding piece 73Cbp provided at one end of the positioning holder 72C can be disposed. The groove 84 penetrates both surfaces of the cam plate 80, but may be a bottomed groove open on the side of the stage 60.

An operating roller 85 is located at the back of the groove 84. The operating roller 85 is a roller rotatably supported around an axis along the sub-scanning direction A2. The operating roller 85 is not in contact with the protruding piece 73Cbp while the stage 60 is located at the setting position P1, and is disposed at a position where the operating roller can be in contact with the protruding piece 73Cbp while the stage 60 is located at the eject position P3. The operating roller 85 may not be provided at the back of the groove 84, and the position itself at the back of a second cam groove may be set to be contactable with the protruding piece 73Cbp while the stage 60 is located at the eject position P3.

The protruding piece 73Cbp is not in contact with the operating roller 85 while the stage 60 is located at the setting position P1 and the reading position P2. In this state, the positioning surface 72CF of the positioning holder 72C is located at a contact position where the IP 10 is supported from below by the weight of the positioning holder 72C or by the biasing member.

When the stage 60 moves from the setting position P1 to the eject position P3, the protruding piece 73Cbp comes into contact with the operating roller 85, and the positioning surface 72CF moves from the contact position to the retreat position. Thus, the IP 10 can slide down from above the supporting surface 64F of the stage 60.

The stage 60 does not need to have the above configuration. For example, on the supporting surface, the entire positioning holder of the IP may be fixed at the fixed position. In addition, the stage may include a positioning holder that supports the IP only from below with respect to the obliquely inclined supporting surface. Furthermore, for example, the stage may have a configuration including a positioning holder that supports the IP only from below and one side with respect to the obliquely inclined supporting surface. The stage may have the supporting surface along the horizontal direction perpendicular to the gravity direction. That is, the stage 60 may have a configuration in which the IP 10 guided by the setting guide 200 is supported by a guide destination.

<Setting Guide>

Figure 9:
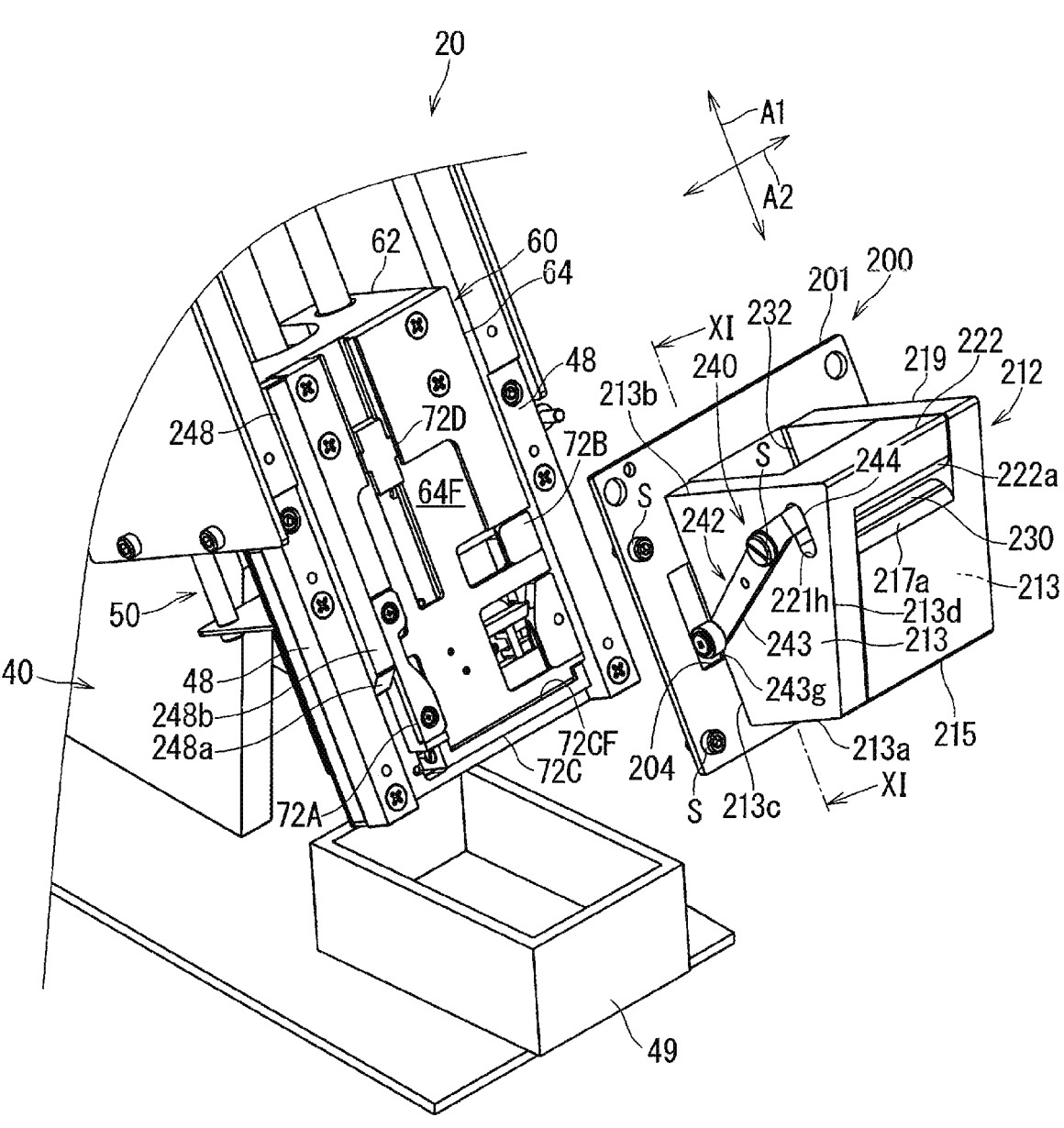
FIG. 9 is a perspective view illustrating a state in which a setting guide is removed from a support member.
Figure 11:
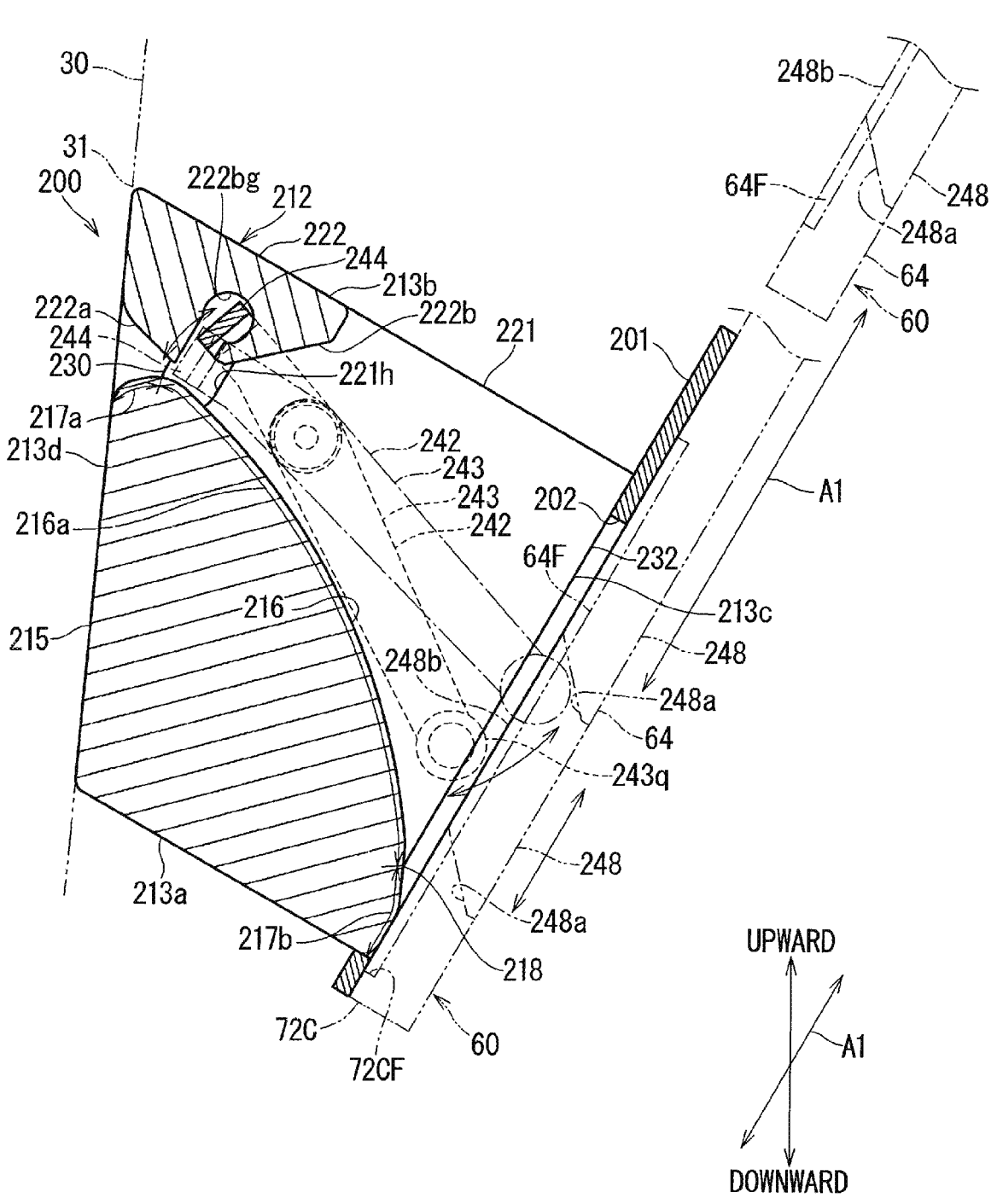
FIG. 11 is an explanatory view illustrating an operation of a shutter.
Figures 12, 13:
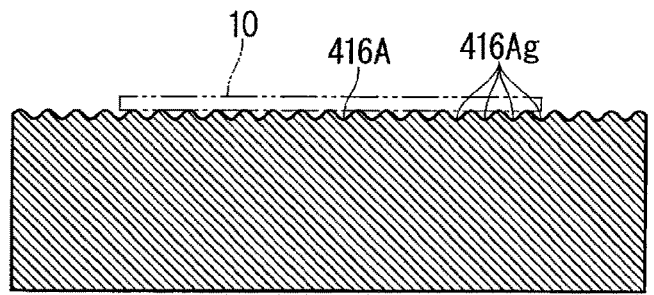
FIG. 12 is an explanatory view illustrating a guiding operation of an IP.
FIG. 13 is a sectional view illustrating an IP guide surface according to a first modification.

FIG. 9 is a perspective view illustrating a state in which the setting guide 200 is removed from the support member 40. FIG. 10 is an exploded perspective view of the setting guide 200. FIG. 11 is an explanatory view illustrating the operation of a shutter 244 in a section taken along a line XI-XI in FIG. 9. FIG. 12 is an explanatory view illustrating a guide operation of the IP 10 in the section taken along the line XI-XI in FIG. 9.

As illustrated in FIGS. 1 to 3, 5, and 9 to 12, the setting guide 200 includes the IP guide surface 216 and guides the IP 10 toward the stage 60. The IP guide surface (first IP guide surface) 216 is a surface inclined downward and a surface guiding the IP 10 obliquely downward. The setting guide 200 is fixed to a portion of the pair of support rods 48 protruding from the lower lateral-direction side plate 46L by screwing or the like. Thus, the setting guide 200 can be opposite to the stage 60 located at the setting position P1 from the side of the supporting surface 64F. The setting guide 200 may be opposed to the stage 60 while the IP 10 to be guided can be guided to the stage 60 at the setting position P1. For this reason, for example, a part of the setting guide 200 may protrude toward the side of the reading position P2 within a range not interfering with the reading unit 90.

More specifically, the setting guide 200 includes a guide base plate 201 and a guide body 212.

The guide base plate 201 is formed in a plate made of metal or resin, in this case, a square plate shape. The width dimension (the dimension in the sub-scanning direction A2) of the guide base plate 201 is set to a size corresponding to the width of the pair of support rods 48, and is fixed to be bridged over the pair of support rods 48. The length of the guide base plate 201 in the main scanning direction A1 is set to the size corresponding to the length of the portion of the pair of support rods 48 protruding from the lower lateral-direction side plate 46L. The guide base plate 201 can cover a portion of the stage 60 protruding from the lower lateral-direction side plate 46L.

A plate passage opening 202 is formed in the guide base plate 201. The plate passage opening 202 is a rectangular opening through which the IP 10 can pass. For example, the plate passage opening 202 is formed in a square shape larger than the size of the IP 10 (the maximum size when the IPs 10 of the plurality of sizes are assumed). The plate passage opening 202 is formed at a position opposite to the supporting surface 64F in the stage 60 located at the setting position P1. The guide base plate 201 may be omitted. For example, the guide body 212 may be directly fixed to the support rod 48.

A shutter operating opening 204 is formed in the guide base plate 201. For example, the shutter operating opening 204 is formed next to the plate passage opening 202. For example, the shutter operating opening 204 is a rectangular opening that is long along the main scanning direction A1.

For example, the guide body 212 is formed of a resin that is easily cleaned and sterilized and has durability. The guide body 212 includes the IP guide surface 216, and guides the IP 10 from the opening 31 of the housing 30 toward the stage 60.

The guide body 212 is formed in a rectangular parallel-epiped shape with two outward surfaces perpendicular to the sub-scanning direction A2 as two bottom surfaces 213.

Each bottom surface 213 is formed in a trapezoidal shape surrounded by an upper base 213*a*, a lower base 213*b* longer than the upper base 213*a*, a side 213*c* perpendicular to the upper base 213*a* and the lower base 213*b* (particularly see FIG. 11), and an oblique side 213*d* extending in an oblique direction with respect to the upper base 213*a* and the lower base 213*b* (particularly see FIG. 11). For convenience of description, reference signs of the respective sides are illustrated in FIGS. 9 and 11.

The surface between the two sides 213*c* of the guide body 212 is opposite to the guide base plate 201 in the posture parallel to the guide base plate 201. In a state where the guide base plate 201 is attached to the pair of support rods 48, between the pair of support rods 48, the surface between two sides 213*c* of the guide body 212 is opposite to the supporting surface 64F of the stage 60 through the plate passage opening 202.

In the guide body 212, the surface between two upper bases 213*a*, the surface between two lower bases 213*b*, and two bottom surfaces are in a vertical posture with respect to the guide base plate 201.

In the guide body 212, the surface between the two oblique sides 213*d* faces the opposite side with respect to the guide base plate 201 in the posture inclined with respect to the guide base plate 201. In the guide body 212, the surface between two oblique sides 213*d* is disposed along the surface of the housing 30 where the opening 31 is formed. In the guide body 212, the surface between two oblique sides 213*d* is exposed to the outside of the housing 30 through the opening 31.

The guide body 212 includes a pair of side wall portions 219, 221, a guide portion 215, and an insertion guide 222.

The pair of side wall portions 219, 221 is a plate portion having the bottom surface 213 as the outward surface, and is arranged in a parallel attitude at an interval.

The guide portion 215 and the insertion guide 222 are disposed between the pair of side wall portions 219.

The guide portion 215 is disposed between the pair of side wall portions 219, 221 and at a position closer to the upper base 213*a* and the oblique side 213*d*. The surface of the guide portion 215 facing obliquely upward on the side of the stage 60 is the IP guide surface 216.

The IP guide surface 216 is formed to gradually face downward toward the supporting surface 64F. In the first embodiment, the IP guide surface 216 includes a portion that is a curved surface 216a protruding outward. In the first embodiment, the entire IP guide surface 216 is the curved surface 216a. The curved surface 216a draws curves that are convex upward and toward the side of the stage 60 when viewed along the sub-scanning direction A2. On the curved surface 216a, the flat IP 10 is less likely to come into surface contact, and thus the IP 10 is less likely to be stuck to the curved surface 216a. For this reason, the IP 10 can smoothly slide down on the curved surface 216a. In addition, because an amount of friction between the curved surface 216a and the IP 10 is reduced, a possibility of damage to the surface of the IP 10 is also reduced.

The upper end of the IP guide surface 216 is positioned above the lower end (for example, the position of the positioning surface 72CF) of the supporting surface 64F in the stage 60, and is positioned above the upper end (for example, the position of the positioning surface 72DF located at the separated position) of the supporting surface 64F. An inlet guide surface 217a extends from the upper end of the IP guide surface 216 toward the direction away from the stage 60. The inlet guide surface 217a is formed in a shape facing downward as it is away from the stage 60. The inlet guide surface 217a guides the IP 10 inserted at the position deviated from the upper end of the IP guide surface 216 toward the upper end of the IP guide surface 216.

The lower end of the IP guide surface 216 is located below the upper end of the IP guide surface 216, located below the upper end (for example, the position of the positioning surface 72DF located at the separated position) of the supporting surface 64F, and located at a height closer to the lower end (for example, the position of the positioning surface 72CF) than the upper end of the supporting surface 64F.

In the first preferred embodiment, the top portion of the guide portion 215 that protrudes most toward the side of the stage 60 in the horizontal direction is a front-back inverting portion 218. Consequently, the front-back inverting portion 218 is continuous to the downstream side of the IP guide surface 216 in a guiding direction of the IP 10. The front-back inverting portion 218 will be further described later in relation to the supporting surface 64F of the stage 60.

A restricting guide surface 217b extends further downward from the lower end of the IP guide surface 216. The restricting guide surface 217b is continuous with the front-back inverting portion 218 on the side of the positioning holder 72C.

The restricting guide surface 217b is formed in a shape gradually approaching the supporting surface 64F (inclined surface) as it goes downward in an inclination direction of the supporting surface 64F (inclined surface). In the first embodiment, the upper portion of the restricting guide surface 217b is continuously connected to the front-back inverting portion 218 and formed as a curved surface that protrudes outward. That is, the IP guide surface 216, the front-back inverting portion 218, and the restricting guide surface 217b are continuously formed in this order. The lower portion of the restricting guide surface 217b is formed in the plane along the supporting surface 64F (inclined surface). A lower portion of the restricting guide surface 217b is close to the positioning holder 72C while positioning surface 72CF is located at the contact position.

Thus, it is difficult to form a gap into which the IP 10 enters between the restricting guide surface 217b and the positioning holder 72C.

The insertion guide 222 is positioned above the upper end of the IP guide surface 216 and the inlet guide surface 217a. The portion of the insertion guide 222 opposite to the inlet guide surface 217a is formed on the insertion guide surface 222a opposite to the upper inlet guide surface 217a at an interval. The insertion guide surface 222a is directed in the direction away from the inlet guide surface 217a as it is away from the stage 60. The distance between the inlet guide surface 217a and the insertion guide surface 222a gradually increases with distance from the stage 60.

The inlet guide surface 217a, the insertion guide surface 222a, and the inner surfaces of the pair of side wall portions 219, 221 form the insertion port 230 feeding the IP 10 to the upper end of the IP guide surface 216.

The insertion port 230 is formed in the size through which the IP 10 can pass. That is, the insertion guide surface 222a is separated from the upper end of the IP guide surface 216 by a distance corresponding to the thickness of an IP 10. Thus, a minimum slit width W (see FIG. 12) of the insertion port 230 is set to the size corresponding to the thickness T of the IP 10. For example, the slit width W may be set to the size obtained by adding about 1 mm to the thickness T of the IP 10. For example, when the IP 10 stores the radiation image, sometimes a protector may be attached to the IP 10 from the viewpoint of mechanical protection of the IP 10, suppression of loss of X-ray information, and the like. When the slit width W is set to the size corresponding to the thickness T of the IP 10, the IP 10 covered with the protector is hardly inserted into the insertion port 230. For this reason, the IP 10 with the protector attached is prevented from being erroneously inserted into the scanner 20.

When the IP 10 to be read by the scanner 20 has a plurality of sizes, a length L (width in the longitudinal direction) of the insertion port 230 is set to the size that allows the IP 10 having the largest width to pass therethrough. It is conceivable that the thickness T of the IP 10 is the same even when the size of the IP 10 is different. So, as described above, when the erroneous insertion of the IP 10 with the protector attached can be prevented by setting the size of the slit width W of the insertion port 230, the above-described erroneous insertion can be reduced while the reading of the IPs 10 of various sizes is enabled. In addition, a freedom degree of the input allowable width of the IP 10 can be limited when the IP 10 is inserted into the insertion port 230. For this reason, because the insertion position of the IP 10 into the inside of the scanner 20 is limited, inadvertent misalignment or falling off on the stage 60 is hardly generated.

The dimensions of the insertion port 230 and the IP guide surface 216 in the direction along the sub-scanning direction A2 (horizontal direction) are larger than the dimension of the IP 10 in the lateral direction. In addition, a distance larger than the dimension in the longitudinal direction of the IP 10 is separated between the upper end of the IP guide surface 216 and the supporting surface 64F. Thus, the setting guide 200 can guide the IP 10 in the posture in which the longitudinal direction of the IP 10 is along the moving direction of the IP 10 on the IP guide surface 216. In other words, the setting guide 200 can guide the IP 10 toward the stage 60 in the posture in which the lateral direction of the IP 10 is along the sub-scanning direction A2 (horizontal direction).

As described above, the stage may support the IP in the posture in which the lateral direction of the IP is inclined with respect to the horizontal direction. In this case, the setting guide is guided toward the stage in the posture in which the lateral direction of the IP is along the horizontal direction.

A retreat surface 222b directed upward toward the stage 60 is continuous with the end of the insertion guide 222 on the side of the stage 60 with respect to the insertion guide surface 222a.

A retreat groove 222bg is formed in a portion of the retreat surface 222b of the insertion guide 222. The retreat groove 222bg is formed in an elongated groove shape extending along the sub-scanning direction A2 while being open to the side of the IP guide surface 216. The shutter 244 to be described later can retreat to the IP guide surface 216.

An opening 232 facing the supporting surface 64F of the stage 60 is formed on the surface between the two sides 213c of the guide body 212. The IP 10 sliding down the IP guide surface 216 can reach the supporting surface 64F of the stage 60 through the opening 232. In each figure, an opening is drawn above the guide body 212. The opening is an opening for description, and is actually closed.

In the first embodiment, the guide body 212 has a two-split configuration of a guide split body 214 including the guide portion 215 and one of side wall portions 219, and a guide split body 220 including the insertion guide 222 and the other side wall portion 221 (see FIG. 10). Because the guide body 212 has the split structure, the IP guide surface 216, the insertion guide surface 222a, and the like can be easily processed into an arbitrary shape. A specific configuration example forming the guide body 212 is not limited to this example. The entire guide body may be configured by one part, or the guide body may be divided by any number and at any boundary. For example, the portion forming the inlet guide surface 217a and the portion forming the curved surface 216a may be split.

The guide split bodies 214, 220 are fixed to the guide base plate 201 with screws S or the like while surfaces of the side wall portions 219, 221 of the guide split bodies 214, 220 on the side of the side 213c are in surface contact with the guide base plate 201. When the guide split bodies 214, 220 are fixed to the guide base plate 201, the guide split bodies 214, 220 are kept in a combined state. The configuration in which the setting guide 200 is supported at the fixed position is not limited to the above example. As described in a later modification, the setting guide may be slidably fitted and fixed to the scanner.

The guide body 212 or the guide 200 is configured to be detachable from the support member 40. In this case, even when the input IP 10 is clogged in the scanner 20, the user can easily access the clogged IP 10 by removing the guide body 212 or the guide 200. Thus, the clogging of the IP 10 can be easily eliminated. For example, the portion including the guide insertion port 230 may be configured to be detachable from the housing.

In the first embodiment, the guide base plate 201 protrudes outward from the guide body 212. The setting guide 200 is detachably attached to the pair of support rods 48 while both side portions of the guide base plate 201 protruding outward from the guide body 212 are overlapped on the pair of support rods 48. The position where the setting guide 200 is attached to the pair of support rods 48 is a guiding position where the setting guide 200 guides the IP 10 toward the stage 60. In the first embodiment, the screw S penetrates the guide base plate 201 and is fastened to the screw holes of the pair of support rods 48. The setting guide 200 is attached to the pair of support rods 48 by tightening the screw S. The setting guide 200 is removed from the pair of support rods 48 by loosening the screw S to remove the screw S from the support rod 48.

The configuration in which the setting guide 200 is detachably attached to the support member 40 including the support rod 48 is not limited to the above example. For example, the setting guide 200 may be detachably attached to the support member 40 by locking a locking member using an elastic member such as a spring to the setting guide 200. That is, when the setting guide 200 can be removed from the predetermined guide position and returned to the original guide position without irreversible damage of the scanner 20, it can be said that the setting guide 200 is detachable from the guide position.

The entire setting guide 200 is not necessarily detachable. It is sufficient that at least a part of the setting guide 200 is detachable, and at least a part of the IP guide surface 16 is exposed to the outside (outside the housing) while the at least the part is removed. When the portion including the IP guide surface 216 in contact with the IP 10 is detachable, cleaning is easy.

The setting guide 200 includes the shutter 244 that openably closes the insertion port 230. The shutter 244 is a part of the shutter mechanism 240 that operates in conjunction with the movement of the stage 60.

That is, the shutter mechanism 240 includes a swing member 242. The swing member 242 is a member in which a swing body 243 and the shutter 244 are connected in an L shape. The swing body 243 is swingably supported by an outer surface of one side wall portion 221. For example, the swing body 243 is swingably supported with respect to the side wall portion 221 by the screw S. The shutter 244 is connected to one end of the swing body 243. A through-hole 221h penetrating the retreat groove 222bg is formed in the one side wall portion 221 (see FIGS. 10 to 12). The through-hole 221h is formed as an elongated hole extending from the retreat groove 222bg toward the side of the IP guide surface 216. The shutter 244 penetrates the through-hole 221h and is disposed between the pair of side wall portions 219, 221. In response to the swing of the swing body 243, the shutter 244 is supported to be able to reciprocate between the closed position (indicated by a two-dot chain line in FIG. 11) located between the upper end of the IP guide surface 216 and the insertion guide 222 and an open position (indicated by a solid line in FIG. 11) located in the retreat groove 222bg.

The other end of the swing body 243 extends from the side wall portion 221 to the side of the side 213c. In accordance with the swing of the swing body 243, the other end of the swing body 243 is movably supported between the protruding position protruding from the side 213c and the retreat position approaching the side of the side 213c. The shutter 244 is located at the closed position while the other end of the swing body 243 is located at the protruding position. The shutter 244 is located at the open position while the other end of the swing body 243 is located at the retreat position.

The swing member 242 is always biased such that the shutter 244 moves from the open position to the closed position. For example, the swing shaft of the swing member 242 is set closer to the other end of the swing body 243 than the gravity center of the swing body 243, whereby the swing member 242 is biased in the above direction by gravity. The swing member 242 may be biased in the above direction by a spring such as a separately provided torsion coil spring.

In the first embodiment, a roller 243q is rotatably supported at the other end of the swing body 243. Because the roller 243q comes into contact with a shutter cam 248, frictional force between the other end of the swing body 243 and the shutter cam 248 is reduced. The other end of the swing body 243 may be in direct contact with the shutter cam 248.

The swing member 242 swings when the stage 60 moves to the setting position P1. At this point, while the stage 60 is located at the setting position P1, the shutter 244 moves to the open position, and the shutter 244 moves to the closed position while the stage 60 moves from the setting position P1 to the reading position P2 (before the reading of the IP 10 starts).

That is, the shutter mechanism 240 includes the shutter cam 248 that moves together with the stage 60 (see FIGS. 6, 9, and 11). For example, the shutter cam 248 may be a member supported by the plate portion 64, a member supported by the movable support 62, or a portion integrated with the plate portion 64.

The shutter cam 248 is a long portion along the main scanning direction A1 on one side of the plate portion 64. In the sub-scanning direction A2, the shutter cam 248 is located at the position where the shutter cam 248 can come into contact with the other end of the swing member 242.

The shutter cam 248 has an operating surface 248*a* that faces the direction away from the setting guide 200 as it goes from the reading position P2 toward the setting position P1 along the main scanning direction A1, and an open state maintaining surface 248*b* that faces the setting guide 200 along both the main scanning direction A1 and the sub-scanning direction A2. The operating surface 248*a* is located closer to (lower side) the setting position P1. The open state maintaining surface 248*b* extends from the operating surface 248*a* toward the side (upper side) of the reading position P2.

When the stage 60 is located at the setting position P1, the roller 243*q* at the other end of the swing member 242 is in a state of being raised up the open state maintaining surface 248*b* of the shutter cam 248. For this reason, the other end of the swing member 242 is located at the retreat position, and the shutter 244 is located at the open position in the retreat groove 222*bg*.

In this state, the insertion port 230 is open, and the IP 10 can be inserted into the IP guide surface 216 through the insertion port 230.

When the stage 60 moves from the setting position P1 to the reading position P2, the shutter cam 248 moves toward the side of the reading position P2. When the operating surface 248*a* reaches the other end position of the swing member 242, the other end of the swing member 242 moves from the open state maintaining surface 248*b* to the protruding position along the operating surface 248*a* by the biasing force acting on the swing member 242. Thus, the shutter 244 moves to the closed position. When the stage 60 further moves toward the side of the reading position P2, the state in which the shutter 244 is located at the closed position is maintained by the biasing force always acting on the swing member 242.

When the stage 60 returns to the setting position P1, the roller 243*q* at the other end of the swing member 242 moves from the operating surface 248*a* onto the open state maintaining surface 248*b* to a raise-up retreat position. Thus, the shutter 244 moves to the open position in the retreat groove 222*bg*, the insertion port 230 is opened, and the shutter 244 returns to the above state.

In the first embodiment, the example in which the shutter 244 is open and closed using the movement of the stage 60 is described. The shutter 244 may be driven by a drive unit (for example, a motor or a solenoid actuator) different from the motor 53 that moves the stage 60.

The housing 30 covers the setting guide 200, the support member 40, the stage 60, the reading unit 90, and the like while the surface between the pair of oblique sides 213*d* of the setting guide 200 is exposed through the opening 31 (see FIG. 1). For this reason, the housing 30 covers the reading unit 90 including the stage 60, the excitation light source 92, and the photodetector 94, at least the IP guide surface 216 and the front-back inverting portion 218 in the setting guide 200, and the supporting surface 64F (inclined surface).

<Configuration in which the IP is Guided Toward the Stage while being Reversed>

Hereinafter, a description will be given focusing on a configuration in which the IP 10 is guided toward the stage 60 while being reversed. At this point, reversing the IP 10 means changing the orientation to change one surface facing upward of the IP 10 to the other surface regardless of whether the IP 10 is in the horizontal posture or the inclined posture.

At least one of the setting guide 200 and the stage 60 includes the inclined surface. The inclined surface is a surface that is inclined downward to the opposite side with respect to the IP guide surface 216 and receives the IP 10 guided by the IP guide surface 216 to guide the IP 10 obliquely downward, i.e. the inclined surface and the IP guide surface 216 oppose each other and the inclined surface is inclined such as to extend towards the IP guide surface 216 in a downward direction.

In the first embodiment, the stage 60 includes the inclined surface. More specifically, the supporting surface 64F of the stage 60 is the inclined surface. That is, the IP guide surface 216 is directed downward toward the side of the stage 60, and the supporting surface 64F is directed downward toward the side of the setting guide 200. In other words, the IP guide surface 216 and the supporting surface 64F are inclined downward to different sides. For this reason, the supporting surface 64F is inclined downward to the opposite side with respect to the IP guide surface 216. Furthermore, the supporting surface 64F spreads on a downward extension of a tangent line of each part of the IP guide surface 216 when viewed along the sub-scanning direction A2. For this reason, the supporting surface 64F spreads in the region where the IP 10 guided downward by the IP guide surface 216 can be received downward according to gravity. Thus, the supporting surface 64F is an example of the inclined surface.

At least one of the stage 60 and the setting guide 200 includes the front-back inverting portion 218 that comes into contact with the IP 10 guided by the supporting surface 64F (inclined surface) from the front surface 10*a* side of the IP 10 to invert the IP 10 to the same inclined posture as the supporting surface 64F (inclined surface). For example, the front-back inverting portion 218 may be located closer to the uppermost end of the supporting surface 64F (inclined surface) than the lowermost end of the supporting surface 64F (inclined surface) in the horizontal direction. In this case, it is conceivable that the lower end of the IP 10 may further slide down on the supporting surface 64F (inclined surface) when the IP 10 sliding down on the IP guide surface 216 reaches the supporting surface 64F (inclined surface). Then, when the lower end of the IP 10 slides down beyond the front-back inverting portion 218 in the horizontal direction, the inclination state of the IP 10 is reversed. Thus, the IP 10 is inverted and supported on the supporting surface 64F (inclined surface).

In the first embodiment, the stage 60 includes a receiving surface that receives the IP 10 supported by the supporting surface 64F (inclined surface) from the lower side in the inclination direction of the supporting surface 64F (inclined surface). Because the lower positioning surface 72CF receives the IP 10 from below, the lower positioning surface 72CF is the receiving surface.

In relation to the positioning surface 72CF (receiving surface), the front-back inverting portion 218 is a portion in which the positioning surface 72CF (receiving surface) is located closer to the supporting surface 64F (inclined surface) than the extension just above the position where the IP 10 is received. In FIG. 12, an extension line L1 just above the positioning surface 72CF (receiving surface) and an extension line L2 just below the front-back inverting portion 218 are illustrated. A distance between L1 and L2 in the horizontal direction is a position difference D of the front-back inverting portion 218 with respect to the positioning surface 72CF (receiving surface) in the horizontal direction. When the position difference D exceeds 0, the inclination of the IP 10 can be reversed. As the position difference D increases, the opposite side inclination angle of the IP 10 can be increased, and the IP 10 can be easily inverted. The portion as the front-back inverting portion 218 may be any portion that can be in contact with the IP 10, and may be a greatly spreading surface or a linear portion.

In the case where the positioning surface 72CF is inclined with respect to the gravity direction or the like, it is sufficient that the front-back inverting portion 218 is located closer to the supporting surface 64F than the position just above the extension of the position with reference to the position where the positioning surface 72CF receives the IP 10 on the supporting surface 64F.

<Guide Operation>

The guiding operation of the IP 10 by the setting guide 200 will be described mainly with reference to FIG. 12.

The IP 10 is inserted into the insertion port 230 in the posture in which the longitudinal direction of the IP 10 intersects (perpendicular to) the extending direction of the insertion port 230 (see Q1). The insertion end of the IP 10 is guided by the inlet guide surface 217a and the insertion guide surface 222a to the portion of the insertion port 230 narrowest between the guide portion 215 and the insertion guide 222. When the protector is still attached to the IP 10, the thickness including the protector exceeds the width W of the insertion port 230, so that the IP 10 is less likely to penetrate deeper than the insertion port 230.

The IP 10 goes beyond the insertion port 230 and is further inserted into the back (see Q2). When more than half of the IP 10 is positioned on the IP guide surface 216 beyond the insertion port 230, the IP 10 slides down according to the inclination of the IP guide surface 216 due to gravity without being pressed by a hand. Eventually, the lower end of the IP 10 reaches the supporting surface 64F (inclined surface) (see Q3). The lower end of the IP 10 further slides downward according to the inclination of the supporting surface 64F (inclined surface).

The portion of the IP 10 that is in contact with the front-back inverting portion 218 above the lower end is kept at the position on the line L2, and restricted from moving to the side of the line L1 in the horizontal direction (see Q4). For this reason, when the lower end of the IP 10 moves downward from the line L1 toward the side of the line L2 according to the inclination of the supporting surface 64F (inclined surface), the inclination posture becomes opposite to that in the previous state. That is, before the lower end of the IP 10 exceeds the line L1, the IP 10 is inclined in the same direction as the IP guide surface 216. When the lower end of the IP 10 exceeds the line L1 to approach the line L2, the IP 10 is inclined in the same direction as the supporting surface 64F (inclined surface). Then, the gravity center of the IP 10 is biased to the side of the supporting surface 64F (inclined surface) opposite to the line L1 with respect to the lower end of the IP 10. Thus, the IP 10 is further inclined such that the back surface of the IP 10 approaches the side of the supporting surface 64F (inclined surface). Thus, the supporting surface 64F (inclined surface) of the stage 60 can come into contact with the back surface 10b of the IP 10 to hold the IP 10 in the same inclined posture as the supporting surface 64F (inclined surface) (see Q5).

<Reading Operation>

An operation example of the scanner 20 will be described.

In an initial state, the stage 60 is located at the setting position P1 (see FIGS. 1, 4, and 5). In this state, the positioning surfaces 72AF, 72BF are open in the sub-scanning direction A2 (horizontal direction). The positioning surfaces 72CF, 72DF are open in the main scanning direction A1. Furthermore, because the protruding piece 73Cbp does not come into contact with the operating roller 85, the positioning surface 72CF of the positioning holder 72C is located at a contact position where the IP 10 is supported from below.

In addition, because the roller 243q at the other end of the swing member 242 is raised on the open state maintaining surface 248b, the shutter 244 moves to the open position in the retreat groove 222bg, and the insertion port 230 is in the opened state.

In this state, the IP 10 is inserted into the insertion port 230 of the setting guide 200 (see FIG. 12). The IP 10 is inserted into the insertion port 230 in the posture in which the radiation image forming layer 11 (the front surface 10a of the IP 10) faces downward. In general, sunlight is irradiated from the sky. An indoor lighting fixture is irradiated from above such as a ceiling. The scanner 20 is assumed to be installed on a table or the like. For this reason, most of the sunlight and the illumination light in the environment where the scanner is installed is assumed to be emitted to the scanner 20 from above. When the radiation image forming layer 11 of the IP 10 faces downward, the radiation image forming layer 11 is less likely to be inadvertently exposed to the sunlight and the illumination light.

The IP 10 inserted into the setting guide 200 is supported on the stage 60 in an inverted state by cooperation of the IP guide surface 216 and the supporting surface 64F (inclined surface) in the setting guide 200. On the supporting surface 64F (inclined surface) of the stage 60, the back surface 10b of the IP 10 faces downward in the gravity direction, and the radiation image forming layer 11 faces upward in the gravity direction. For this reason, the stage 60 can mainly support the IP 10 by its own weight of the IP 10.

When instruction to perform the reading by the scanner 20 is input, a controller 100 (see FIG. 3) moves the stage 60 from the setting position P1 toward the reading position P2 by the driving of the stage moving mechanism 50.

During the movement, the positioning holder 72B approaches the positioning holder 72A, and the positioning holder 72B and the positioning holder 72A sandwich both side edge portions of the IP 10 from both right and left sides.

When the stage 60 moves from the setting position P1 to the reading position P2, the positioning holder 72D approaches the positioning holder 72C. Thus, the pair of positioning surfaces 72CF, 72DF sandwiches the upper and lower edge portions of the IP 10 from above and below.

Thus, the IP 10 is positioned and held in both the main scanning direction A1 and the sub-scanning direction A2 on the supporting surface 64F (inclined surface) of the stage 60.

In addition, while the stage 60 is moving from the setting position P1 to the reading position P2, the roller 243q at the other end of the swing member 242 goes down from the open state maintaining surface 248*b* through the operating surface 248*a*. Thus, the shutter 244 comes out of the retreat groove 222*bg* and moves to the closed position, and the insertion port 230 is closed. When the stage 60 moves from the setting position P1 to the reading position P2, the insertion port 230 is closed, so that erroneous insertion of the plurality of IPs 10 into the insertion port 230 is prevented.

When the stage 60 moves to the reading position P2, the reading unit 90 reads a latent image of the IP 10.

After the reading by the reading unit 90 is completed, the stage 60 returns to the setting position P1. During the movement, the operation opposite to the above is performed, and the holding of the IP 10 on the stage 60 is released. In addition, the shutter 244 moves to the open position, and the insertion port 230 is open.

When the stage 60 moves from the setting position P1 toward the eject position P3, the protruding piece 73Cbp comes into contact with the operating roller 85, and the positioning surface 72CF of the positioning holder 72C moves from the contact position to the retreat position (see FIG. 8). The IP 10 supported on the positioning surface 72CF slides down from the supporting surface 64F (inclined surface) through the positioning surface 72CF, and is collected in the recover tray 49. Depending on the attitude of the retreat position of the positioning surface 72CF and the design of how to retreat, the IP 10 may be collected in the recover tray 49 without passing through (not contacting with) the positioning surface 72CF in a process of sliding down.

Thereafter, the stage 60 returns from the eject position P3 to the setting position P1. Then, the positioning holder 72C rotationally moves such that the positioning surface 72CF returns to the contact position. In this state, as described above, the IP 10 can be set on the stage 60 at the setting position P1.

<Effect>

According to the radiation image scanner 20 configured as described above, when the IP 10 is set in the scanner 20, the radiation image forming surface of the IP 10 is less likely to be exposed to external light.

That is, it is assumed that the intensity of light from above such as sunlight and ceiling illumination light is the strongest around the scanner 20. According to the scanner 20, the IP 10 can be placed on the IP guide surface 216 in the housing 30 with the front surface 10*a* as the radiation image forming surface facing downward. Accordingly, the radiation image forming surface of the IP 10 is less likely to be exposed to external light during the placement. The IP 10 is guided obliquely downward by the IP guide surface 216, received by the supporting surface 64F (inclined surface) inclined downward to the side opposite to the IP guide surface 216, and further guided obliquely downward. When the IP 10 is guided obliquely downward by the supporting surface 64F (inclined surface), the front-back inverting portion 218 comes into contact with the IP 10 from the side of the front surface 10*a* to invert the IP 10 to the same inclined posture as the supporting surface 64F (inclined surface). For this reason, the IP 10 is supported by the stage 60 in the posture, in which the front and back surfaces of the IP 10 are vertically inverted and the radiation image forming surface faces upward. In other words, the front and back surfaces of the IP 10 are inverted with respect to the positional relationship at the time of insertion. Thus, when the IP 10 is set in the radiation image scanner 20, the IP 10 is less likely to be exposed to external light, and can be supported on the stage 60 in the posture in which the radiation image forming surface of the IP 10 always faces upward, so that the reading is smoothly started.

In addition, the supporting surface 64F of the stage 60 is the inclined surface, the stage 60 includes the positioning surface 72CF as the receiving surface that receives the IP 10 from below, and the setting guide 200 includes the front-back inverting portion 218. For this reason, the IP 10 can be inverted using the supporting surface 64F of the stage 60 as the inclined surface, and the configuration can be simplified.

In addition, because the front-back inverting portion 218 is provided on the side of the IP 10, it is possible to reliably exert an inversion action while abutting on the IP 10 to be inverted, and the front-back inverting portion 218 is less likely to be an obstacle when the IP 10 on the stage 60 is read.

The stage 60, the excitation light source 92, the photo-detector 94, the IP guide surface 216, the front-back inverting portion 218, and the supporting surface 64F (inclined surface) are covered with the housing 30. For this reason, the IP 10 is inverted and set on the stage 60 in the housing 30. For this reason, the radiation image forming surface of the IP 10 is hardly exposed to external light.

The IP guide surface 216 includes the curved surface 216*a* protruding outward. For this reason, the IP 10 is less likely to come into surface contact with the IP guide surface 216, and the IP 10 is less likely to remain on the IP guide surface 216. Thus, the IP guide surface 216 can more reliably guide the IP 10 toward the stage 60.

The front-back inverting portion 218 is continuous with the IP guide surface 216 on the downstream side in the guiding direction of the IP 10. For this reason, the IP 10 is hardly caught between the IP guide surface 216 and the front-back inverting portion 218, and the IP 10 is smoothly guided toward the stage 60. In addition, the IP 10 can be smoothly guided toward the stage 60 using falling force of the IP 10 sliding down by a certain distance in the gravity direction.

In addition, the setting guide 200 includes the restricting guide surface 217*b* that approaches the supporting surface 64F (inclined surface) as it goes downward in the inclination direction of the supporting surface 64F (inclined surface). For this reason, the IP 10, particularly the lower end of the IP 10 is more reliably guided toward the supporting surface 64F (inclined surface) by the restricting guide surface 217*b*.

The restricting guide surface 217*b* is continuous with the front-back inverting portion 218 on the side of the positioning surface 72CF (receiving surface). For this reason, the IP 10 is less likely to be caught between the front-back inverting portion 218 and the restricting guide surface 217*b*.

The setting guide 200 includes the insertion guide 222 located at a distance corresponding to the thickness of the IP 10 with respect to the upper end of the IP guide surface 216. For this reason, when the IP 10 is inserted between the upper end of the IP guide surface 216 and the insertion guide 222, the IP 10 is easily set on the IP guide surface 216 such that the back surface 10*b* of the IP 10 is aligned with the IP guide surface 216.

The setting guide 200 is detachably attached to the support member 40. The cleaning and sterilization treatment of the setting guide 200 can be easily performed by removing at least a part of the setting guide 200. In addition, even when a defect such as clogging of the IP 10 is generated, the defect is easily solved by removing the setting guide 200. For example, the setting guide 200 may be removed from the support member 40 while the housing 30 is removed.

The setting guide 200 includes the shutter 244 that openably closes the insertion port 230. For this reason, it is possible to regulate the timing at which the IP 10 can be inserted. For example, the shutter 244 is opened while the stage 60 is located at the setting position P1, and the shutter 244 is closed in the middle of movement from the setting position P1 to the reading position P2. Thus, the shutter 244 is prevented from being additionally input while the IP 10 is being read. In addition, while the shutter 244 is closed, it is possible to shut out a trace amount of external light that may enter from the insertion port 230, so that it is possible to implement an environment in which incidence of external light is more highly managed in the image reading of the IP 10.

The setting guide 200 guides the IP 10 in the posture in which the longitudinal direction of the IP 10 is along the moving direction of the IP 10 on the IP guide surface 216, and the stage 60 supports the IP 10 in the posture in which the longitudinal direction of the IP 10 is inclined with respect to the horizontal direction. For this reason, the IP 10 can be easily tilted largely by the front-back inverting portion 218 as compared with the case where the lateral direction of the IP 10 is aligned with the horizontal direction. In other words, when the IP 10 is inclined by the front-back inverting portion 218, the positional deviation of the gravity center of the IP 10 from the lower end of the IP 10 can be increased. For this reason, the IP 10 is easily inverted more reliably.

Furthermore, because the setting guide 200 faces the stage 60 located at the setting position P1, the setting guide 200 can be easily disposed without interfering with the excitation light source 92 and the photodetector 94.

<Modifications>

In the first embodiment, the description is made assuming that the IP guide surface 216 is the surface in which portions having the same height are continuous along the width direction (sub-scanning direction A2). That is, when the IP guide surface 216 is observed in the section along the width direction (sub-scanning direction A2) and intersecting the IP guide surface 216, the IP guide surface 216 is represented by a straight line.

Figures 14, 15:
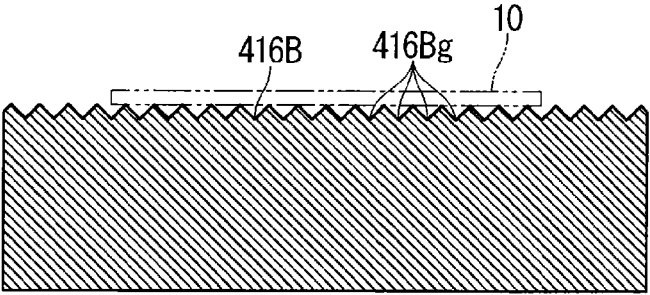
FIG. 14 is a sectional view illustrating an IP guide surface according to a second modification.
FIG. 15 is a sectional view illustrating a setting guide according to a third modification.

Like an IP guide surface 416A according to a first modification in FIG. 13 or an IP guide surface 416B according to a second modification in FIG. 14, the IP guide surfaces 416A, 416B may be surfaces that are uneven in the width direction.

On the IP guide surface 416A, a plurality of grooves 416Ag are formed in parallel. Each groove 416Ag is a groove extending along the guiding direction of the IP 10 by the IP guide surface 416A. The groove 416Ag includes a curved bottom and a curved opening. For this reason, in the section along the width direction (sub-scanning direction A2) of the IP guide surface 416A and intersecting the IP guide surface 416A, the IP guide surface 416A is expressed by a curved wave (for example, a sine curve).

On the IP guide surface 416B, a plurality of grooves 416Bg are formed in parallel. Each groove 416Bg is a groove extending along the guiding direction of the IP 10 by the IP guide surface 416B. The groove 416Bg is a V-shaped groove in which the bottom forms an angle. The wall between the adjacent grooves 416Bg is formed as a triangular ridge in which an apex forms a corner. For this reason, in the section along the width direction (sub-scanning direction A2) of the IP guide surface 416B and intersecting the IP guide surface 416B, the IP guide surface 416B is expressed in a shape in which a triangular wave is continuous.

According to these IP guide surfaces 416A, 416B, the IP guide surfaces 416A, 416B and the IP 10 are less likely to come into surface contact with each other, so that the IP 10 is less likely to stick to the IP guide surfaces 416A, 416B. For this reason, the IP 10 is smoothly guided by the IP guide surfaces 416A, 416B.

In addition, when the IP 10 slides down toward the stage 60, the IP 10 is less likely to be caught by unevennesses formed by the grooves 416Ag, 416Bg. When trying to be laterally displaced, the IP 10 may be caught by the unevennesses due to the grooves 416Ag, 416Bg, so that the lateral displacement of the IP 10 is prevented. The height difference between the unevennesses of the plurality of grooves 416Ag, 416Bg is desirably designed to be smaller than the thickness of the IP 10 because the possibility that the IP 10 is clogged with the unevenness is reduced.

As in a setting guide 500A according to a third modification in FIG. 15, an IP guide surface 516A corresponding to the IP guide surface 216 may be configured by the combination of a plurality of planes 516Af1, 516Af2. Here, the plane 516Af1 is inclined downward from the insertion port 230 toward the stage 60, and the plane 516Af2 is connected to the lower edge of the plane 516Af1 at a corner. The plane 516Af2 is inclined more than the plane 516Af1.

A front-back inverting portion 518A corresponding to the front-back inverting portion 218 is located on a lower edge of the plane 516Af2.

A restricting guide surface 517Ab corresponding to the restricting guide surface 217b is connected to the lower side of the front-back inverting portion 518A. In the third modification, the restricting guide surface 517Ab is a plane, and gradually approaches the supporting surface 64F (inclined surface) of the stage 60 as it goes downward.

Also in the third modification, the IP 10 is guided toward the stage 60 by the planes 516Af1, 516Af2. When the lower end of the IP 10 comes into contact with the supporting surface 64F (inclined surface) and slides downward, the intermediate portion of the IP 10 comes into contact with the front-back inverting portion 518A, and the IP 10 is inverted. Then, the IP 10 is supported on the stage 60 while the back surface 10b of the IP 10 is in contact with the supporting surface 64F (inclined surface).

The IP guide surface may be configured by a combination of at least three planes.

Figure 16:
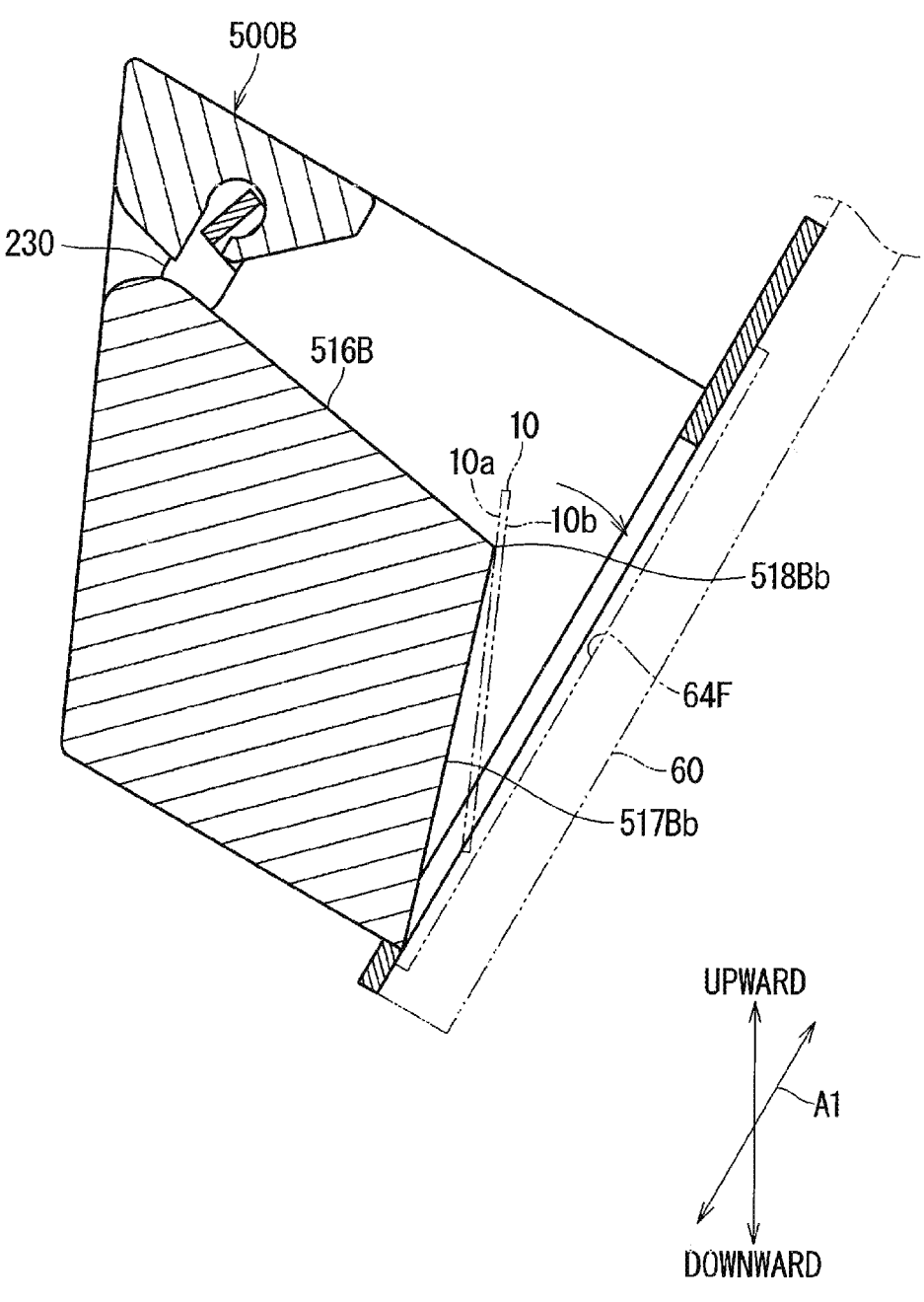
FIG. 16 is a sectional view illustrating a setting guide according to a fourth modification.

As in a setting guide 500B according to a fourth modification in FIG. 16, an IP guide surface 516B corresponding to the IP guide surface 216 may be one plane. At this point, the IP guide surface 516B that is the plane is inclined downward from the insertion port 230 toward the stage 60.

A front-back inverting portion 518Bb corresponding to the front-back inverting portion 218 is located at a lower edge of the IP guide surface 516B.

A restricting guide surface 517Bb corresponding to the restricting guide surface 217b is continuous below the front-back inverting portion 518Bb. In the fourth modification, the restricting guide surface 517B is a plane, and takes the posture gradually approaching the supporting surface 64F (inclined surface) of the stage 60 as it goes downward.

Also in the fourth modification, the IP 10 is guided toward the stage 60 by the IP guide surface 516B. When the lower end of the IP 10 comes into contact with the supporting surface 64F (inclined surface) and slides downward, the intermediate portion of the IP 10 comes into contact with the front-back inverting portion 518Bb, and the IP 10 is inverted. Then, the IP 10 is supported on the stage 60 while the back surface 10b of the IP 10 is in contact with the supporting surface 64F (inclined surface).

As in a setting guide 500C according to a fifth modification in FIG. 17, an IP guide surface 516C corresponding to the IP guide surface 216 may be one plane. At this point, the IP guide surface 516C that is a plane is inclined downward from the insertion port 230 toward the stage 60.

In the fifth modification, the IP guide surface 516C is an upward surface of the plate 515. A front-back inverting portion 518Cb corresponding to the front-back inverting portion 218 is located at the lower edge of the IP guide surface 516C, namely, the lower edge of the plate 515.

In the fifth modification, the restricting guide surface is omitted.

Also in the fifth modification, similarly to the fourth modification, the IP 10 is guided from the IP guide surface 516C toward the stage 60, inverted, and held on the stage 60.

As illustrated in these modifications, the IP guide surfaces 516A, 516B, 516C may be a plurality of planes 516Af1, 516Af2 or one plane 516B, 516C. In this case, the IP guide surfaces 516A, 516B, 516C can be easily processed as compared with the case of curved surface processing.

Considering the case where the grooves are formed in the IP guide surface along the guiding direction, when the IP guide surface has a shape of one straight line or a combination of a plurality of straight lines when viewed along the horizontal direction orthogonal to the guiding direction of the IP, the processing thereof can be easily performed.

Even when the front-back inverting portions 518A, 518Bb, 518Cb are linear portions or planes, the processing can be easily performed. When the restricting guide surfaces 517Ab, 517B are planes, it can be understood that the processing of the restricting guide surfaces 517Ab, 517B can be easily performed.

Similarly to the above, when the front-back inverting portion has a point or a linear shape or the restricting guide surface has a linear shape as viewed along the horizontal direction orthogonal to the guiding direction of the IP, it can be grasped that processing thereof can be easily performed.

The IP guide surface may be any surface inclined downward. The IP guide surface may be only a curved surface, only a plane, a combination of a curved surface and a plane, a combination of a plane and a plane, or the like.

In the first embodiment, the example in which the supporting surface 64F of the stage 60 is the inclined surface is described. The inclined surface is not necessarily the supporting surface 64F, but the setting guide may have the inclined surface.

Figure 18:
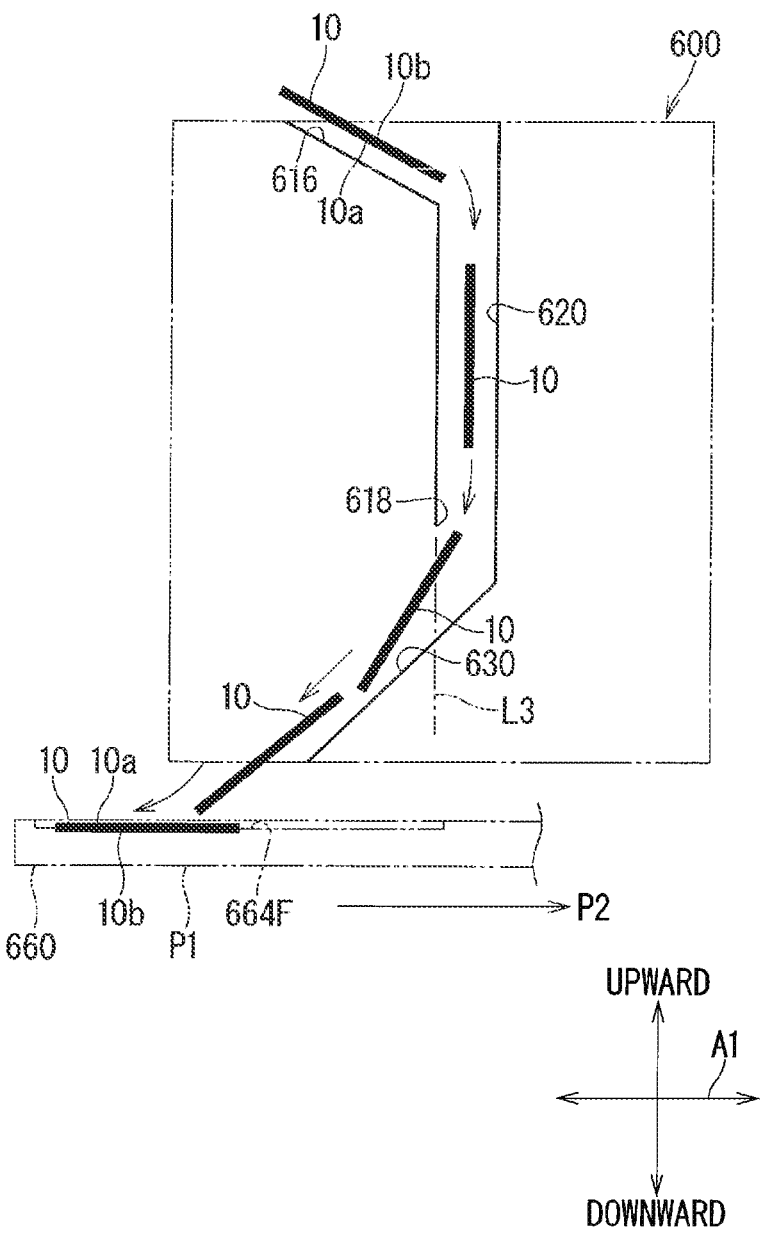
FIG. 18 is an explanatory view illustrating a setting guide according to a sixth modification.

A setting guide 600 according to a sixth modification in FIG. 18 has an IP guide surface 616 inclined downward. A front-back inverting portion 618 extends downward from the IP guide surface 616.

An opposing guide surface 620 is positioned at an interval with respect to the front-back inverting portion 618. The opposing guide surface 620 is parallel to the front-back inverting portion 618.

An inclined surface 630 is connected to a lower end of the opposing guide surface 620. The inclined surface 630 is inclined downward to the opposite side with respect to the IP guide surface 616.

A stage 660 corresponding to the stage 60 is positioned below the extension of the inclined surface 630. The stage 660 has a supporting surface 664F along the horizontal direction. The stage 660 moves from the setting position P1 along the horizontal direction toward the reading position P2.

The IP 10 guided by the IP guide surface 616 falls downward by gravity and is received by the inclined surface 630. The IP 10 is guided obliquely downward by the inclined surface 630 and directed onto the stage 660.

When the IP 10 is guided obliquely downward by the inclined surface 630, the lower end of the IP 10 goes over a lower extension line L3 of the front-back inverting portion 618. For this reason, even when the IP 10 falls on the inclined surface 630 in the same inclination direction as the IP guide surface 616, the lower end of the IP 10 goes beyond the lower extension line L3 of the front-back inverting portion 618 while the portion of the position above the lower end of the IP 10 is regulated by the front-back inverting portion 618, whereby the IP 10 is inverted such that the inclination is reversed. The IP 10 slides down from the inclined surface 630 onto the stage 660 while being inverted.

Thus, even when the setting guide 600 includes the inclined surface 630, the IP 10 can be inverted and set on the stage 660.

In the sixth modification, the planar front-back inverting portion 618 may be omitted, and the linear front-back inverting portion may be located at the lower end of the IP guide surface 616. In this case, the opposing guide surface 620 may be omitted, the distance between the IP guide surface 616 and the inclined surface 630 may be shortened, and the IP 10 guided by the IP guide surface 616 may slide directly onto the inclined surface 630.

When the setting guide 600 includes the inclined surface 630 and the front-back inverting portion 618 as in the sixth modification, the inclined surface and the front-back inverting portion may not be provided on the stage 660. Thus, it is not necessary to tilt the stage 660, and restrictions on the design of the stage 660 and the like can be reduced. The present disclosure can also be applied to a conventional horizontal scanner as disclosed in Patent Document 1.

When the inclined surface is provided on the stage side, the inclined surface may be a supporting surface 664F (see the example of the first embodiment) or exist separately from the supporting surface 664F. In this case, the inclined surface configured by the surface of the member moving together with the stage 60 may be provided at the position, in which the IP 10 sliding down from the IP guide surface can be received and the IP 10 can be guided toward the supporting surface 664F.

Figure 19:
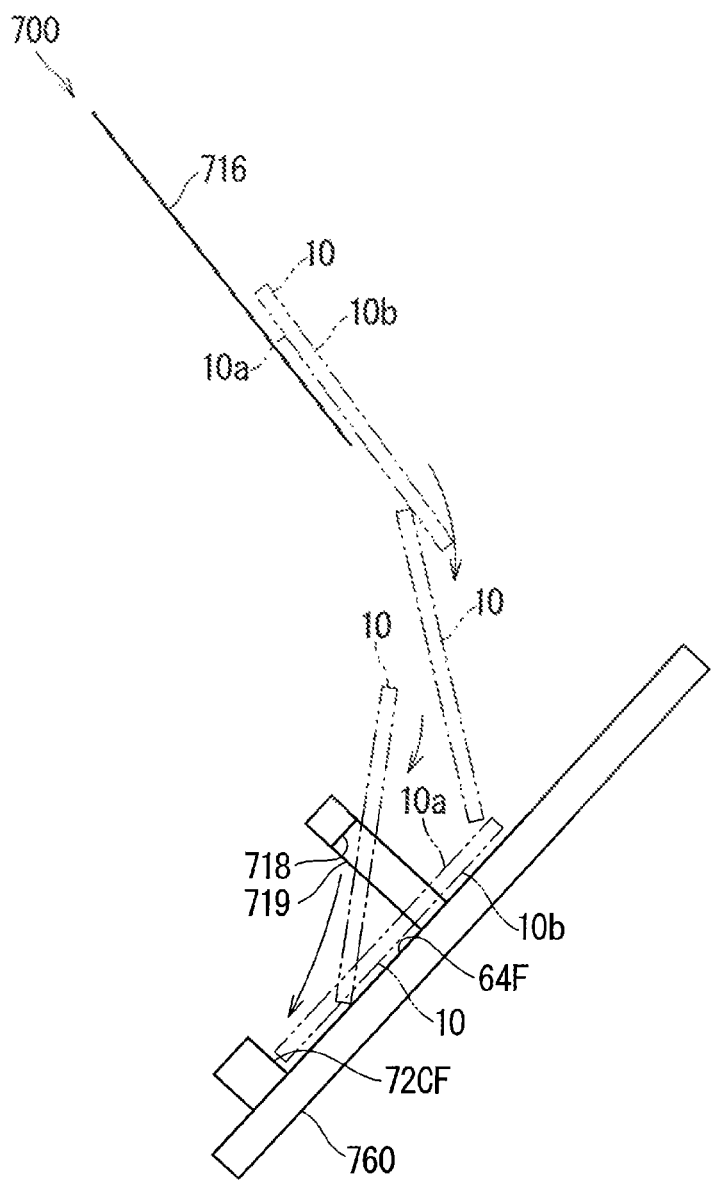
FIG. 19 is an explanatory view illustrating a setting guide according to a seventh modification.

As in a stage 760 according to a seventh modification in FIG. 19, the stage 760 may include a front-back inverting portion 718.

In the seventh modification, an IP guide surface 716 is separated from the supporting surface 64F (inclined surface). The IP 10 is separated from the IP guide surface 716 while the lower end of the IP 10 reaches the supporting surface 64F (inclined surface) from the IP guide surface 716. The front-back inverting portion is omitted on the lower side of the IP 10. For this reason, the front-back inverting portion is omitted on the side of a setting guide 700.

In the seventh modification, the front-back inverting portion 718, which is separated from the supporting surface 64F and extends along the sub-scanning direction A2, is located above the supporting surface 64F (inclined surface) of the stage 760. The front-back inverting portion 718 is supported at the position away from the supporting surface 64F (inclined surface) by a support column 719 or the like protruding from the stage 760. The front-back inverting portion 718 is located above the positioning surface 72CF that is the receiving surface.

In this case, when the lower end of the IP 10 reaches the supporting surface 64F (inclined surface) and slides down on the supporting surface 64F (inclined surface), the portion of the IP 10 above the lower end comes into contact with the front-back inverting portion 718 and is inverted. In the inverted state, the IP 10 further slides down on the supporting surface 64F (inclined surface), reaches the positioning surface 72CF, and is supported on the stage 760.

When the reading unit 90 reads the IP 10, the reading unit 90 may read the IP 10 at the position away from the stage 760 while avoiding the front-back inverting portion 718, data of the front-back inverting portion 718 read in the image processing process may be subjected to arithmetic processing (editing or erasing), or the front-back inverting portion 718 may be retreated and moved by a cam mechanism, another drive mechanism, or the like while the stage 760 moves to the reading position P2.

Second Embodiment

Figure 20:
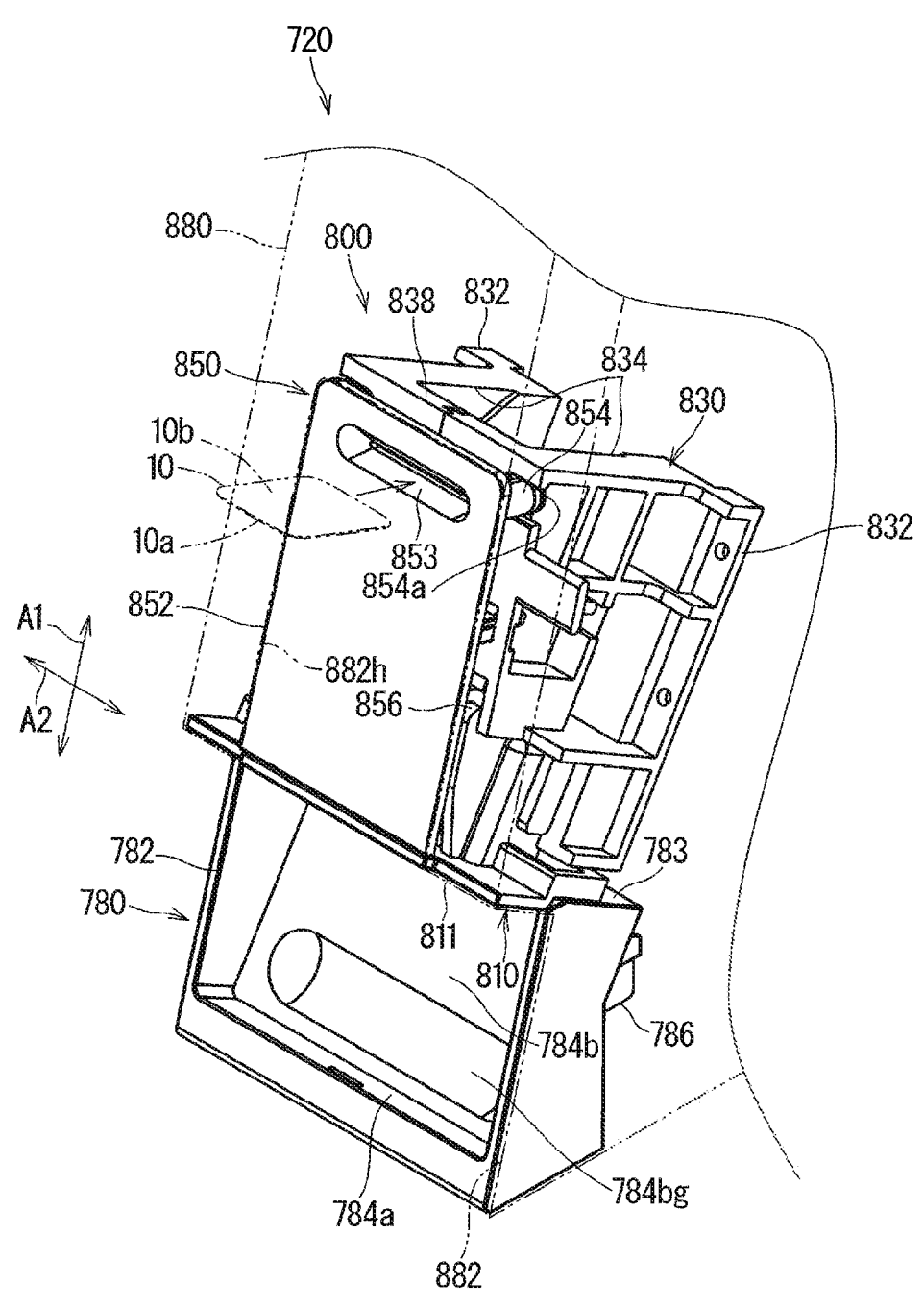
FIG. 20 is a partially perspective view illustrating a scanner according to a second embodiment.
Figure 21:
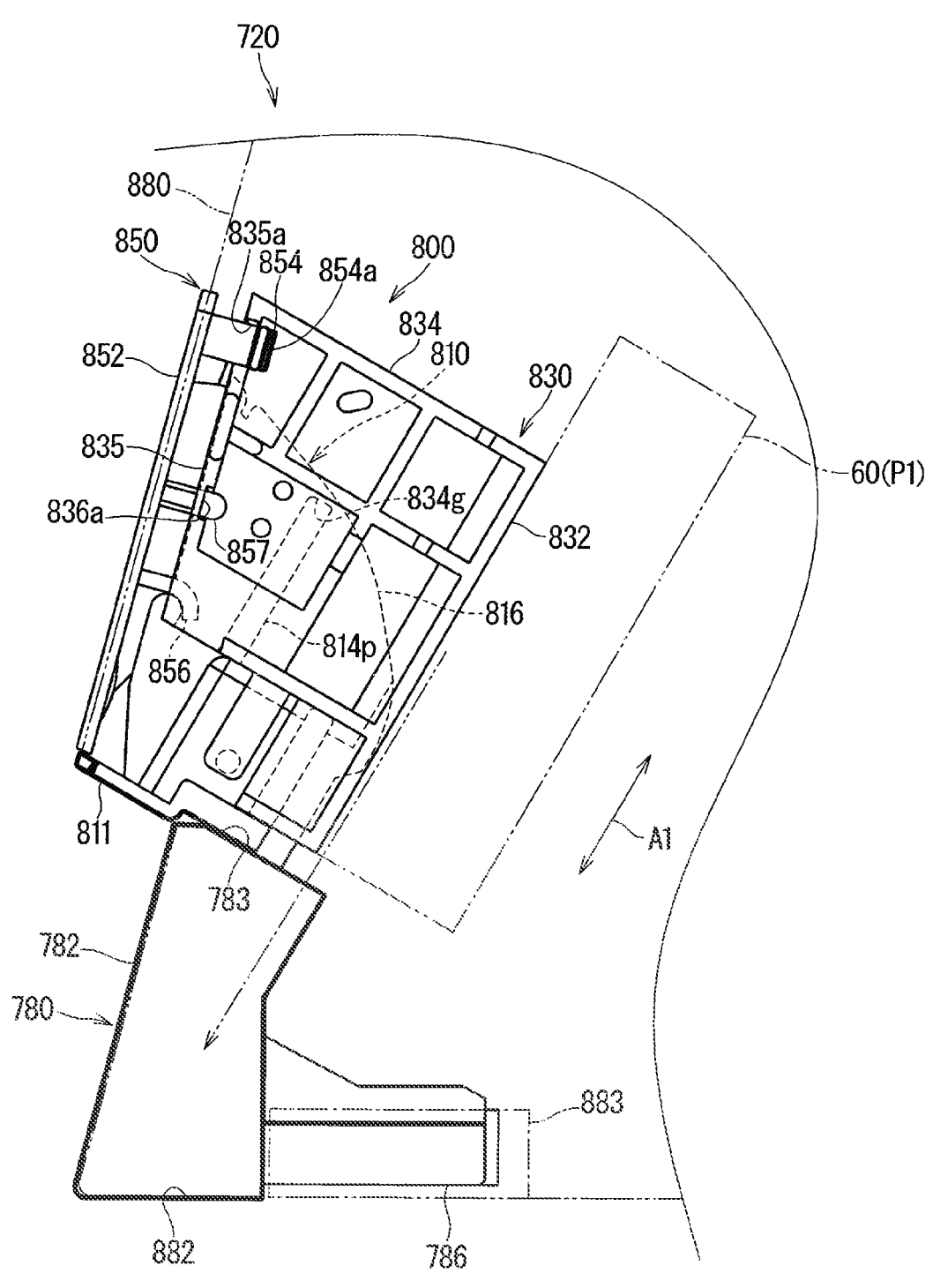
FIG. 21 is a partial side view illustrating the scanner.
Figure 22:
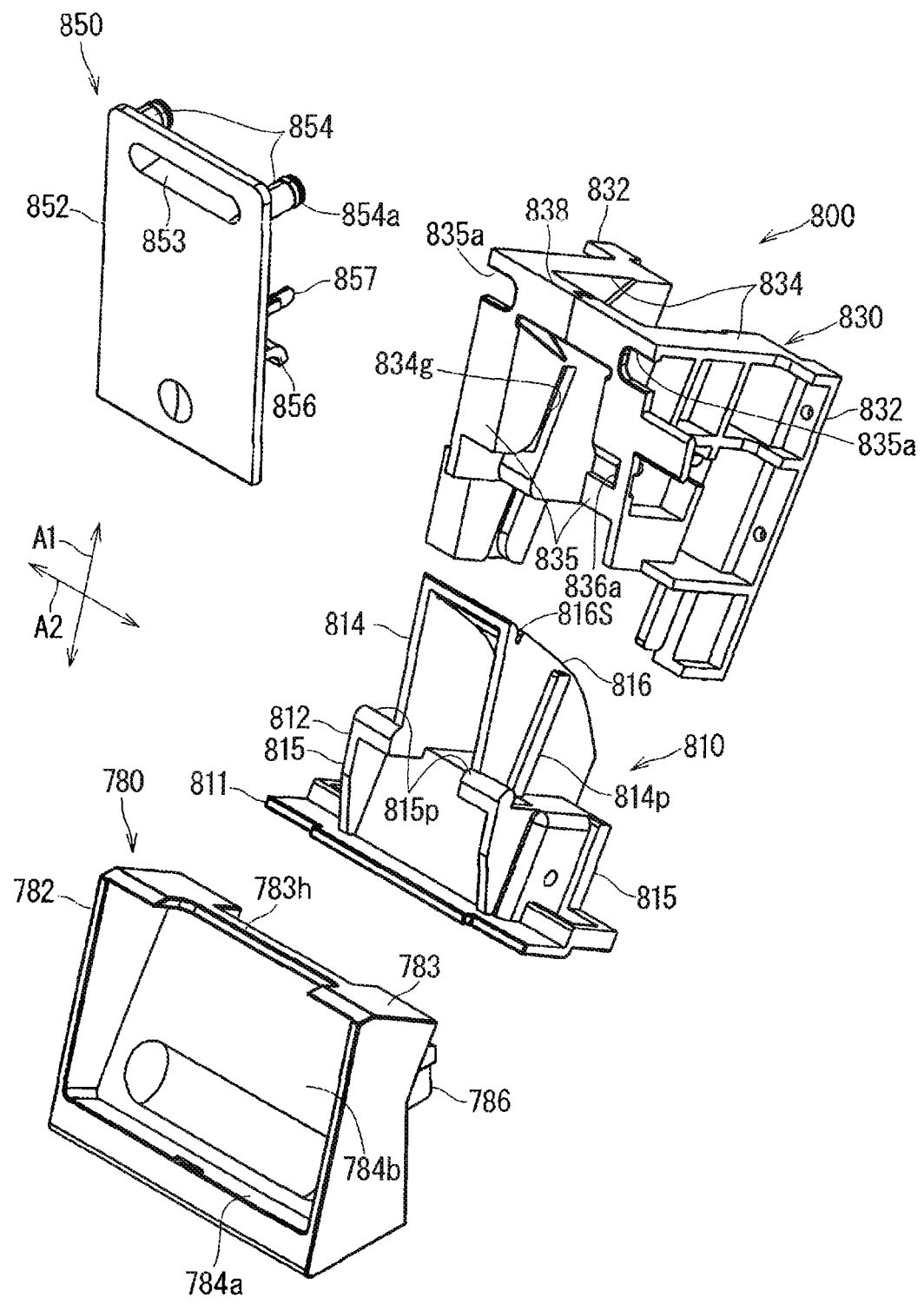
FIG. 22 is an exploded perspective view illustrating a setting guide according to the second embodiment.

A radiation image scanner 720 according to a second embodiment will be described below. FIG. 20 is a schematic perspective view illustrating a scanner 720. FIG. 21 is a partially side view illustrating the scanner 720. FIGS. 20 and 21 illustrate a portion of the scanner 720 in which a setting guide 800 is incorporated. FIG. 22 is an exploded perspective view illustrating the setting guide 800 of the second embodiment.

A main difference between the scanner 720 and the scanner 20 of the first embodiment is a configuration related to the setting guide 800 corresponding to the setting guide 200. The setting guide 800 according to the difference will be mainly described.

The setting guide 800 includes a guide body 810, a guide support 830, and a lid portion 850.

The guide support 830 is supported at the fixed position in a housing 880 corresponding to the housing 30. The guide body 810 is a portion including a IP guide surface 816 corresponding to the IP guide surface 216. The guide body 810 is detachably supported by the guide support 830. While the guide body 810 is supported by the guide support 830, the guide body 810 is disposed at the position opposite to the stage 60 located at the setting position P1. In this state, the IP guide surface 816 of the guide body 810 can guide the IP 10 input from the outside toward the stage 60 while inverting the IP. When the guide body 810 is removed from the guide support 830, the IP guide surface 816 can be exposed to the outside.

The lid portion 850 covers an outward portion of the housing 880 of the guide body 810 from the outside. A joint or the like between the guide support 830 and the guide body 810 is hidden from the outside by the lid portion 850, and external light hardly enters the inside of the scanner 720. The lid portion 850 may be omitted. The lid portion 850 may be integrated with the guide body 810.

Each part of the setting guide 800 will be described more specifically.

The guide support 830 includes a pair of base portions 832, a pair of side wall portions 834, and an intermediate connection portion 838. In the second embodiment, the guide support 830 is formed of a resin component split into two in the width direction. The entire guide support 830 may be integrally molded with resin or the like.

Each of the pair of base portions 832 is an elongated portion and is arranged in parallel at an interval. The pair of base portions 832 is supported at the fixed position in the housing 880. For example, the pair of base portions 832 is fixed to the pair of support rods 48 by screwing or the like (see FIG. 9).

The pair of side wall portions 834 is supported in an erected state with respect to the pair of base portions 832. The space between the pair of side wall portions 834 spreads forward of the stage 60 located at the setting position P1.

The guide body 810 can be opposite to the stage 60 located at the setting position P1 by disposing the guide body 810 in the space.

In the second embodiment, the interval between the upper portions of the pair of side wall portions 834 is larger than the interval between the lower portions. The pair of base portions 832 may be integrally joined in advance by adhesion or the like before being supported in the housing 880. Similarly, the pair of side wall portions 834 may be integrally joined in advance by adhesion or the like. Similarly, one of the pair of base portions 832 and one of the pair of side wall portions 834 may be integrally joined in advance by adhesion or the like.

A slide holding groove 834g is formed on the inner surfaces of the pair of side wall portions 834. In the second embodiment, the slide holding groove 834g extends toward a recover tray 780 described later in the upper portion of the pair of side wall portions 834. More specifically, the slide holding groove 834g is a bottomed groove extending along the main scanning direction A1. The lower end of the slide holding groove 834g on the side of the recover tray 780 is open. The upper end of the slide holding groove 834g opposite to the recover tray 780 is a closed end that is not open. The slide holding groove 834g may extend linearly or may be bent in the middle. For example, the middle of the slide holding groove 834g may be bent in a crank shape, and a pair of slide holding protrusions 814p may be hooked on the middle of the slide holding groove 834g. This makes it difficult to easily separate the guide body 810 and the guide support 830.

A pair of lid supports 835 is provided in an upper portion of a tip of the pair of side wall portions 834. The outward surface of the lid support 835 is located inside the outward surface of the housing 880. The outward surface of the lid support 835 is along the direction parallel to the outward surface of the housing 880.

A recess 835a into which an attachment protrusion 854 of the lid portion 850 is fitted is formed in the lid support 835.

A space below the pair of lid supports 835 is a space open outward of the housing 880. A claw portion 856 of the lid portion 850 is disposed in this space.

The intermediate connection portion 838 is an elongated portion extending in the direction connecting the pair of side wall portions 834. Similarly to the insertion guide surface 222a, the intermediate connection portion 838 includes a surface located away from the upper end of the IP guide surface 816 by a distance corresponding to the thickness of the IP 10. An insertion port 839 is formed by the upper end edge of the IP guide surface 816 and the intermediate connection portion 838.

The guide support 830 may be supported at the fixed position in the housing 880, and the configuration in which the guide support is supported is not limited to the above example. For example, the guide support 830 may be directly fixed to the housing 880.

Figure 23:
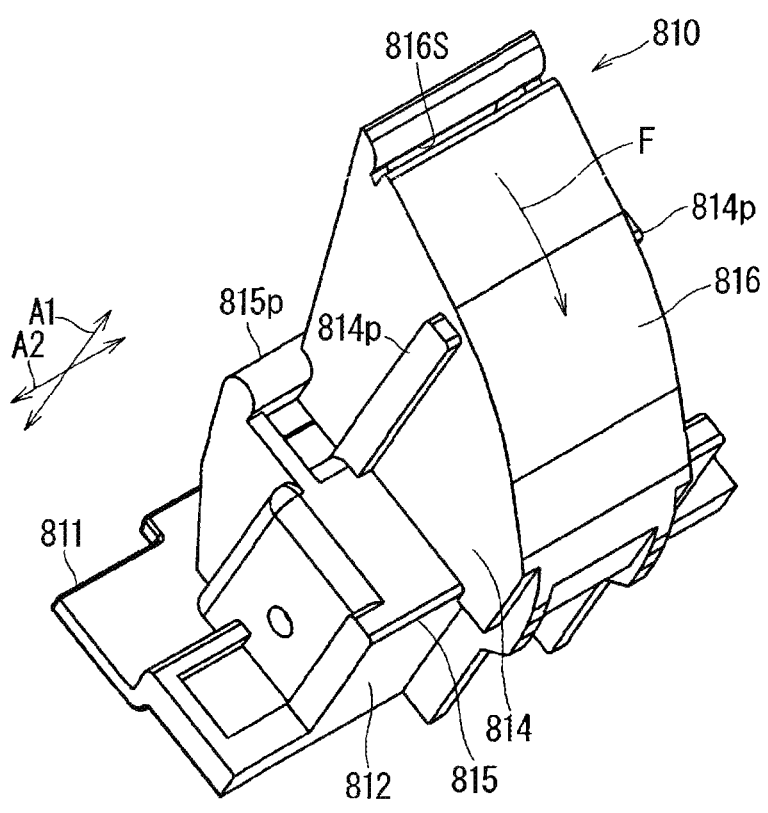
FIG. 23 is a perspective view illustrating a guide body as viewed from an IP guide surface side.

FIG. 23 is a perspective view illustrating the guide body 810 as viewed from the side of the IP guide surface 816. As illustrated in FIGS. 20 to 23, the guide body 810 is a member including the IP guide surface 816 corresponding to the IP guide surface 16. For example, the guide body 810 is formed of resin.

More specifically, the guide body 810 includes a base plate portion 811, an intermediate base portion 812, and a guide surface forming portion 814.

The guide surface forming portion 814 is set to a size that can be disposed between narrow upper portions of the pair of side wall portions 834. The intermediate base portion 812 is set to a size that can be disposed between wide lower portions of the pair of side wall portions 834. The guide surface forming portion 814 is located on the upper side of the intermediate base portion 812.

The guide surface forming portion 814 and the intermediate base portion 812 are disposed in the space between the pair of side wall portions 834. In this state, the inner surfaces of the pair of side wall portions 834 come into contact with the outward side surfaces of the guide surface forming portion 814 and the intermediate base portion 812, and the guide body 810 is positioned in the width direction (sub-scanning direction A2).

In addition, a both-side protruding portions 815 of the intermediate base portion 812 projecting outward from the guide surface forming portion 814 is brought into contact with the downward step portion positioned in the middle of the pair of side wall portions 834 in the vertical direction, and the position of the guide body 810 in the upward direction is restricted.

An IP guide surface 816 is formed from an upward portion of the guide surface forming portion 814 to a portion opposite to the stage 60 at the setting position P1. The IP guide surface 816 has the same configuration as the IP guide surface 16 of the first embodiment.

A pair of slide holding protrusions 814$p$ extending along the main scanning direction A1 is formed on both side surfaces of the guide surface forming portion 814. The pair of slide holding protrusions 814$p$ is fitted into the slide holding groove 834$g$ from the lower side along the main scanning direction A1. That is, the guide body 810 is set from below with respect to the guide support 830.

Because the pair of slide holding protrusions 814$p$ is fitted into the slide holding groove 834$g$ while the guide body 810 is set in the guide support 830, the guide body 810 is positioned at the fixed position in the direction orthogonal to the supporting surface 64F of the stage 60 (the direction orthogonal to the main scanning direction A1 and the sub-scanning direction A2).

The guide surface forming portion 814 is open on the side opposite to the IP guide surface 816, but this is not essential.

A pair of lid holding protrusions 815$p$ protrudes from the pair of both-side protruding portions 815 of the intermediate base portion 812. The lid holding protrusion 815$p$ protrudes upward from the upper end of the both-side protruding portion 815 close to the lid portion 850. The lid holding protrusion 815$p$ is disposed at the position spaced apart from the lower edge of the lid support 835. Then, the claw portion 856 of the lid portion 850 enters between the lower edge of the lid support 835 and the lid holding protrusion 815$p$, and can be caught by the lid holding protrusion 815$p$.

The base plate portion 811 is a plate portion protruding outward from the lower edge of the intermediate base portion 812. Because the base plate portion 811 comes into contact with the lower surfaces of the pair of side wall portions 834, the upper position of the guide body 810 with respect to the guide support 830 is more reliably regulated. The upper surface of the recover tray 780 comes into contact with the lower surface of the base plate portion 811 while the recover tray 780 is set in the housing 880. Accordingly, downward falling of the guide body 810 is prevented. The base plate portion 811 may be one component or a component in which a plurality of components are combined.

In the second embodiment, a slit 816S is formed in the IP guide surface 816. The slit 816S is located in the middle of a guide path of the IP 10 by the IP guide surface 816. In the second embodiment, the slit 816S is located near the inlet of the IP guide surface 816. The slit 816S is a slit penetrating from the front surface toward the back surface of the IP guide surface 816. The slit 816S is orthogonal to a guiding direction F of the IP 10 by the IP guide surface 816.

The slit 816S may have a bottomed groove shape that is open to the side of the IP guide surface 816 and is not open to the opposite side. The slit 816S may be along the guiding direction F or be oblique to the guiding direction F.

Because the slit 816S exists in the middle of the IP guide surface 816, even when liquid enters the inlet portion of the IP guide surface 816, the liquid enters the slit 816S. For this reason, the flow of the liquid along the guiding direction of the IP 10 is prevented, and the liquid hardly enters the scanner 720 along the IP guide surface 816. When the slit 816S penetrates from the front surface toward the back surface of the IP guide surface 816, the liquid on the slit 816S is guided to the position away from the IP guide surface 816 through the slit 816S. For this reason, the liquid is less likely to enter the scanner 720. As described later, in the case where the guide body 810 is removed and the IP guide surface 816 is sterilized and cleaned, the liquid or the like is less likely to remain when the slit 816S penetrates from the front surface toward the back surface of the IP guide surface 816.

Figure 24:
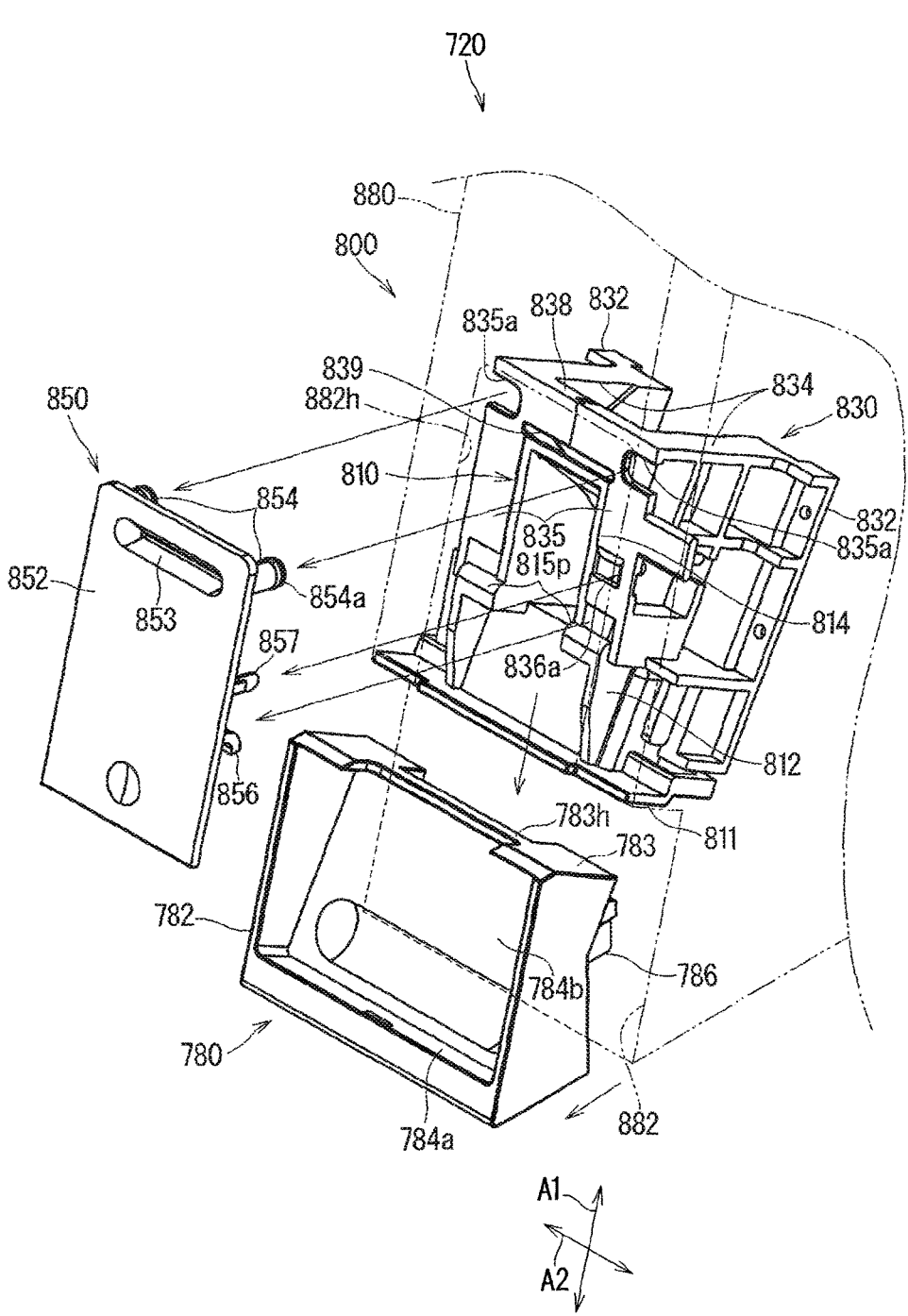
FIG. 24 is a perspective view illustrating a state in which a lid and a tray are removed from a guide support.

FIG. 24 is a perspective view illustrating a state in which the lid portion 850 and the recover tray 780 are removed from the guide support 830. As illustrated in FIGS. 20 to 24, the lid portion 850 includes the lid body 852, the attachment protrusion 854, and the claw portion 856.

The lid body 852 is formed in a plate shape. An opening 882$h$ through which the guide body 810 and the guide support 830 are exposed is formed in the housing 880. The lid body 852 is formed in a plate shape having a size that closes the opening 882$h$.

A lid-side insertion port 853 is formed in the lid body 852. The lid-side insertion port 853 is formed in a slit shape into which the IP 10 can be inserted. The lid-side insertion port 853 is disposed at the position opposite to the insertion port 839 while the lid body 852 disposed in the opening 882$h$.

The attachment protrusion 854 and the claw portion 856 are provided to protrude on the surface of the lid body 852 facing the inside of the housing 880.

The attachment protrusion 854 is formed at the position opposite to the recess 835$a$. The attachment protrusion 854 is formed in a protrusion shape, in this case, a columnar shape that can be inserted into the recess 835$a$. An annular groove is formed at the tip of the attachment protrusion 854, and an annular elastic member 854$a$ such as an O-ring is attached to the annular groove. The attachment protrusion 854 is fitted into the recess 835$a$. In this state, the annular elastic member 854$a$ is caught in the recess 835$a$ from the inside of the housing 880, and the detachment of the attachment protrusion 854 from the recess 835$a$ is prevented. When large force that elastically deforms the annular elastic member 854$a$ is applied, the attachment protrusion 854 can be removed from the recess 835$a$.

The claw portion 856 is formed at the opposite position between the lid support 835 and the lid holding protrusion 815$p$. The claw portion 856 is formed in a hook shape including a portion extending in the direction protruding from the lid body 852 and a portion extending downward from the tip of the portion extending in the direction protruding from the lid body 852. The claw portion 856 is inserted between the lower edge of the lid support 835 and the lid holding protrusion 815$p$, and can be hooked on the lid holding protrusion 815$p$ from above.

In the second embodiment, a guide protrusion 857 protrudes from the lid body 852, and the guide protrusion 857 is guided and inserted into a guide recess 836*a* formed in the guide support 830 when being attached to the lid body 852.

The recover tray 780 is positioned below the setting guide 800 and the stage 60 at the setting position P1. More specifically, a space 882 (see FIGS. 20 and 21) capable of housing the recover tray 780 is formed below the setting guide 800 and the stage 60 at the setting position P1 in the housing 880. In the space 882, a tray setting portion 883 into which a part of the recover tray 780 can be fitted is disposed.

The recover tray 780 includes a tray body 782 and a setting protrusion 786.

The tray body 782 is formed in a rectangular tray shape that is open to the front of the housing 880, namely, to the same side as the lid-side insertion port 853. An upper surface of an upper wall portion 783 of the tray body 782 is formed in a plane extending along the base plate portion 811. An inner portion of the housing 880 in the upper wall portion 783 is located below the stage 60 at the setting position P1. A slit-shaped IP passage port 783*h* is formed on the lower extension of the stage 60 at the setting position P1 in the upper wall portion 783.

A lowermost surface 784*a* in the tray body 782 is along the horizontal direction, and the back side surface in the tray body 782 is an inclined surface 784*b* extending obliquely downward from the IP passage port 783*h*. The IP 10 passed through the IP passage port 783*h* slides on the inclined surface 784*b* and is received on the lowermost surface 784*a*. A sheet that is softer than the tray body 782, such as rubber, may be laid on the lowermost surface 784*a*. In this case, falling impact of the IP 10 can be received by the sheet. In addition, when the sheet is a sheet of rubber or the like that is difficult to slide, the IP 10 is difficult to slide out of the tray body 782.

A recessed groove 784*bg* (see FIG. 20) extending in the horizontal direction is formed in the inclined surface 784*b*. The user can easily take out the IP 10 supported to lean against the inclined surface 784*b* when inserting the fingertip into the recessed groove 784*bg*.

The setting protrusion 786 is formed in a shape extending from the tray body 782 toward the inside of the housing 880. The setting protrusion 786 is fitted into a setting recess formed in the tray setting portion 883 while the recover tray 780 is disposed in the space 882 of the housing 880. Thus, the recover tray 780 is held at the fixed position in the space 882.

In the second embodiment, at least a part of the setting guide 800 is detachable, and at least a part of the IP guide surface 816 is exposed while the at least a part of the setting guide 800 is removed.

In the second embodiment, in a use state of the scanner 720, the guide body 810 is set in the guide support 830 while being positioned between the pair of side wall portions 834. In this state, the pair of slide holding protrusions 814*p* is fitted into the slide holding groove 834*g*.

The attachment protrusion 854 is inserted into the recess 835*a* and the lid portion 850 is attached to the guide support 830 while the claw portion 856 is caught by the lid holding protrusion 815*p*.

Furthermore, the recover tray 780 is set in the space 882 below the guide body 810. In this state, the upper surface of the upper wall portion 783 of the recover tray 780 is in contact with at least a part of the lower surface of the base plate portion 811 of the guide body 810. For this reason, downward removal of the guide body 810 is prevented.

In the above state, the IP guide surface 816 is disposed at the position opposite to the stage 60 located at the setting position P1. For this reason, when the IP 10 is inserted into the lid-side insertion port 853 and the insertion port 839, the IP 10 is guided toward the stage 60 by the IP guide surface 816. At this point, as described in the first embodiment, the IP 10 is inverted. Thus, the IP 10 is set on the stage 60.

After the reading of the IP 10 is completed, the lower positioning holder 72C moves to the retreat position as described in the first embodiment. Then, the IP 10 on the stage 60 slides down. The IP 10 is directed into the recover tray 780 through the IP passage port 783*h*. In the recover tray 780, the IP 10 slides on the inclined surface 784*b* and reaches the lowermost surface 784*a*. In this state, the IP 10 is supported from below by the lowermost surface 784*a* and leans against the inclined surface 784*b*.

For example, when the IP guide surface 816 is sterilized or cleaned, or when the IP 10 is clogged on the IP guide surface 816, the IP guide surface 816 can be exposed to the outside in the following manner.

First, the recover tray 780 is pulled out of the housing 880 (see FIG. 24). Next, the lid portion 850 is removed from the housing 880. At this point, when the lid portion 850 is moved upward after the attachment protrusion 854 on the upper side of the lid portion 850 is moved in the direction of being removed from the recess 835*a*, the hook between the claw portion 856 and the lid holding protrusion 815*p* can be released. Either the recover tray 780 or the lid portion 850 may be removed first.

When the recover tray 780 is removed, the guide body 810 is movable downward into the space 882. When the lid portion 850 is removed, the user can touch the guide body 810 from the front side of the guide body 810.

The user can touch the front portion of the guide body 810 to push down the guide body 810. Then, the guide body 810 moves downward toward the inside of the space 882 while the slide holding protrusion 814*p* moves in the slide holding groove 834*g*. When the slide holding protrusion 814*p* comes out of the slide holding groove 834*g*, the guide body 810 can be removed forward from the housing 880.

When the guide body 810 is removed from the housing 880, the IP guide surface 816 can be exposed to the outside. When at least a part of the IP guide surface 816 is exposed to the outside, it may be understood that the user's finger can touch the IP guide surface 816. Thereby, the IP guide surface 816 can be exposed, or the space extending on the IP guide surface 816 can be accessed from the outside, and the clogged IP 10 can be removed.

By reversing the above, the guide body 810, the lid portion 850, and the recover tray 780 are set in the housing 880.

According to the second embodiment, the radiation image forming surface of the IP 10 is less likely to be exposed to external light by the guide operation of the IP 10 by the IP guide surface 816 when the IP 10 is set in the radiation image scanner 720 similarly to the first embodiment.

According to the second embodiment, at least a part of the setting guide 800 is detachable to expose at least a part of the IP guide surface 816 to the outside. For this reason, even when the defect such as clogging of the IP 10 is generated, it is easy to solve the defect by removing at least a part of the setting guide 800, in this case, the guide body 810. In addition, the IP guide surface 816 and the like can be easily cleaned and sterilized.

In particular, the attachment and detachment of the guide body 810 are performed by the attachment and detachment of the recover tray 780 by the movement of the recover tray 780 and the attachment and detachment of the lid portion

850 by the movement of the lid portion 850. For this reason, the guide body 810 can be easily attached and detached with no use of a tool or the like.

The configuration in which at least a part of the setting guide 800 is detachably supported is not limited to the above example. A locking member using an elastic member such as a spring may be provided in the guide body, and the locking member may be detachably locked to the guide support. The guide body may be detachably attached to the guide support by a screw or the like. The entire setting guide may be detachable from the housing. That is, it can be said that at least a part of the setting guide is detachable as long as at least a part of the setting guide can be detached from the predetermined guiding position and returned to the original guide position without irreversible damage of the scanner 720.

The slit 816S is formed in the middle of the IP guide surface 816. The slit 816S prevents entry of the liquid into the scanner 720. For example, the radiation image scanner of the present invention is used in a hospital of a medical institution such as a hospital or a clinic, and it is also assumed that the radiation image scanner is brought to a visit place such as an individual's home or a facility and used at the time of home medical care. At this point, there is a possibility that the liquid such as a beverage or domestic water is splashed on the scanner 720, and the liquid reaches the IP guide surface 816 through the lid-side insertion port 853 and the insertion port 839 (of course, the possibility as described above can be assumed even in the hospital such as the beverage or the cleaning liquid). Because the liquid enters the slit 816S, the liquid hardly enters deep inside the scanner 720 along the IP guide surface 816.

A plurality of slits may be formed in the IP guide surface. It is not essential that a liquid inflow suppression recess is the slit 816S. The liquid inflow suppression recess may be a hole penetrating from the front surface of the IP guide surface to the back side, or be a recess for temporarily storing the liquid.

Figure 25:
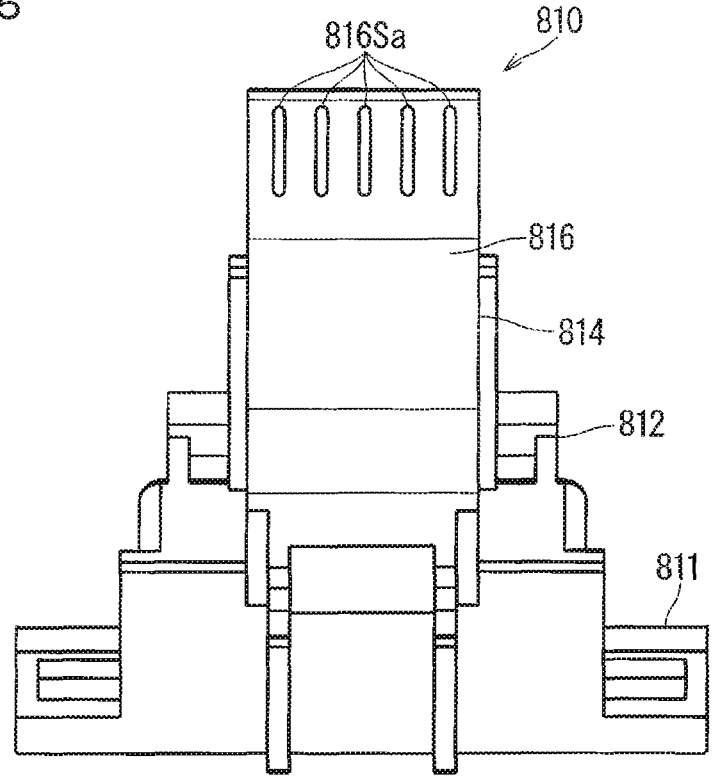
FIG. 25 is a view illustrating a modification of a liquid inflow suppression recess.

As in a modification illustrated in FIG. 25, the liquid inflow suppression recess may be a slit 816Sa formed along the IP guide surface 816. In this case, the IP guide surface 816 may include a plurality of slits 816Sa arranged along the width direction of the IP guide surface 816.

Figure 26:
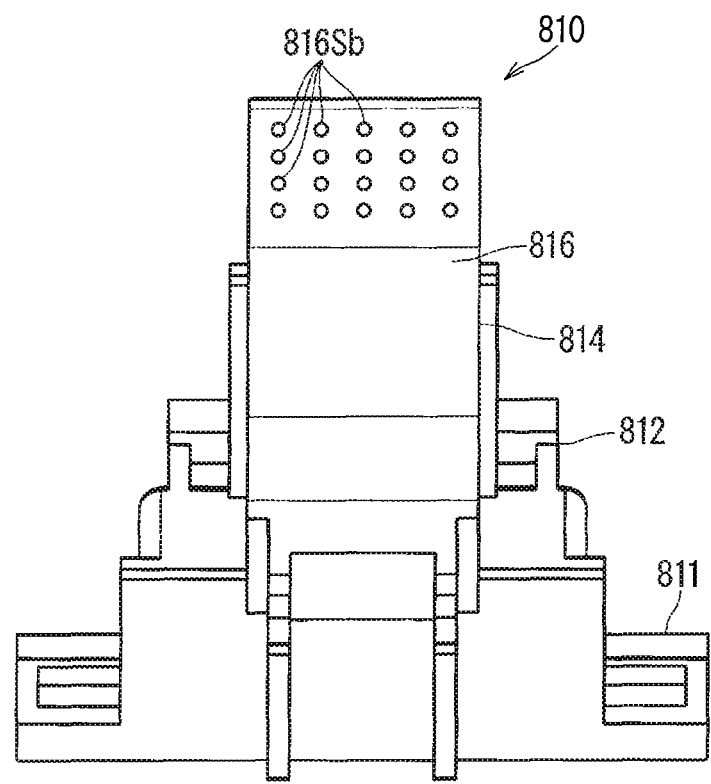
FIG. 26 is a view illustrating another modification of the liquid inflow suppression recess.

As in a modification illustrated in FIG. 26, the liquid inflow suppression recess may be a plurality of holes 816Sb formed in the IP guide surface 816.

In any case, when the IP guide surface 816 is recessed to such an extent that the guide of the IP 10 is not hindered, the liquid is inhibited from flowing on the (front) surface of the IP guide surface 816, and the liquid is less likely to enter the housing 880.

It is not essential that a liquid inflow suppression recess such as the slit 816S is formed in the IP guide surface 816.

The configurations described in the above embodiments and the modifications can appropriately be combined.

Supplementary Note

The present disclosure discloses the following aspects.

A first aspect is a radiation image scanner that reads a radiation image from a front surface of an IP, the radiation image scanner including: a stage that supports the IP from a back surface side; an excitation light source that irradiates the IP supported by the stage with excitation light; a photodetector that detects light emitted from the IP by the excitation light; and a setting guide that guides the IP toward the stage, the setting guide including an IP guide surface that guides the IP obliquely downward, the IP guide surface being inclined downward, at least one of the setting guide and the stage including an inclined surface, the inclined surface being a surface that is inclined downward to an opposite side with respect to the IP guide surface, receives the IP guided by the IP guide surface, and guides the IP obliquely downward, and at least one of the stage and the setting guide including a front-back inverting portion that inverts the IP in an inclined attitude identical to the inclined surface while coming into contact with the IP guided by the inclined surface from a front surface side of the IP.

It is assumed that the intensity of light from above such as sunlight and ceiling illumination light is the strongest around the scanner. According to the scanner, because the IP can be placed on the IP guide surface in the housing while the front surface that is the radiation image forming surface faces downward, the radiation image forming surface of the IP is less likely to be exposed to external light during the placement. The IP is guided obliquely downward by the IP guide surface, received by the inclined surface inclined downward opposite to the IP guide surface, and further guided obliquely downward. When the IP is guided obliquely downward by the inclined surface, the front-back inverting portion comes into contact with the IP from the front surface side to invert the IP to the same inclined posture as the inclined surface. For this reason, the IP is supported by the stage in the posture, in which the front and back surfaces are vertically inverted and the radiation image forming surface faces upward. Thus, when the IP is set in the radiation image scanner, the IP is less likely to be exposed to external light, and can be supported on the stage in the posture in which the radiation image forming surface of the IP is always directed upward, so that the reading is smoothly started.

A second aspect is the radiation image scanner according to the first aspect, in which the stage includes a supporting surface as the inclined surface, the supporting surface being inclined with respect to a horizontal direction and supporting the IP from a back surface side, the stage further includes a receiving surface that receives the IP supported by the supporting surface from a lower side in an inclination direction of the supporting surface, the IP guide surface gradually slopes downward toward the supporting surface and guides the IP toward the supporting surface, the setting guide includes the front-back inverting portion, and the front-back inverting portion is a portion located closer to the supporting surface than an imaginary extension directly above a position where the receiving surface receives the IP.

Because the IP can be inverted using the supporting surface of the stage as the inclined surface, the configuration can be simplified.

A third aspect is the radiation image scanner according to the first aspect, in which the setting guide includes the inclined surface and the front-back inverting portion.

In this case, the supporting surface of the stage may not be inclined.

A fourth aspect is the radiation image scanner according to any one of the first to third aspects, further including a housing that covers the stage, the excitation light source, the photodetector, at least the IP guide surface and the front-back inverting portion of the setting guide, and the inclined surface.

In this case, the IP is inverted and set on the stage in the housing. For this reason, the radiation image forming surface of the IP is hardly exposed to external light.

A fifth aspect is the radiation image scanner according to any one of the first to fourth aspects, in which the IP guide surface includes a portion that is a curved surface protruding outward.

As described above, when the IP guide surface includes the portion that is the curved surface protruding outward, the IP is less likely to come into surface contact with the IP guide surface and is less likely to stay on the IP guide surface.

A sixth aspect is the radiation image scanner according to any one of the first to fourth aspects, in which the IP guide surface has a shape of one straight line or a combination of a plurality of straight lines when viewed along a horizontal direction orthogonal to a guiding direction of the IP.

This facilitates processing of the IP guide surface.

A seventh aspect is the radiation image scanner according to any one of the first to sixth aspects, in which the front-back inverting portion is continuous to a downstream side of a guiding direction of the IP with respect to the IP guide surface.

In this case, the IP is hardly caught between the IP guide surface and the front-back inverting portion.

An eighth aspect is the radiation image scanner according to any one of the first to seventh aspects, in which the setting guide includes a restricting guide surface for the inclined surface that gradually approaches the inclined surface as the restricting guide surface goes downward in an inclination direction of the inclined surface.

In this case, the IP is more reliably guided toward the inclined surface by the restricting guide surface.

A ninth aspect is the radiation image scanner according to the eighth aspect, in which the restricting guide surface is continuous to a downstream side of the front-back inverting portion.

In this case, the IP is hardly caught between the front-back inverting portion and the restricting guide surface.

A tenth aspect is the radiation image scanner according to any one of the first to ninth aspects, in which the setting guide includes an insertion guide positioned away from an upper end of the IP guide surface by a distance corresponding to a thickness of the IP.

In this case, by inserting the IP between the upper end of the IP guide surface and the insertion guide, it is easy to set the IP on the IP guide surface such that the back surface of the IP is along the IP guide surface.

An eleventh aspect is the radiation image scanner according to any one of the first to tenth aspects, in which the setting guide includes a recess that is located halfway of a guide path of the IP by the IP guide surface and suppresses a flow of liquid along a guiding direction of the IP.

Thus, even when the liquid enters the IP guide surface, the recess suppresses the liquid from flowing into the scanner.

A twelfth aspect is the radiation image scanner according to any one of the first to eleventh aspects, in which at least a part of the setting guide is detachably supported such that at least a part of the IP guide surface is exposed outside while being in a detached state.

Thus, the cleaning and sterilization treatment can be easily performed. In addition, even when a defect such as clogging of the IP is generated, it is easy to solve the defect by removing at least a part of the setting guide.

A thirteenth aspect is the radiation image scanner according to any one of the first to twelfth aspects, in which the setting guide includes an insertion port through which the IP is inserted at an upper end of the IP guide surface and a shutter that openably closes the insertion port.

This makes it possible to regulate the timing at which the IP can be inserted. In addition, it is possible to prevent the defect of the radiation image scanner such as plate clogging caused by the insertion of the plurality of IPs into the insertion port.

A fourteenth aspect is the radiation image scanner according to any one of the first to thirteenth aspects, in which the setting guide guides the IP in a posture in which a longitudinal direction of the IP is set along a moving direction of the IP in the IP guide surface, and the stage supports the longitudinal direction of the IP in a posture in which the longitudinal direction of the IP is inclined with respect to a horizontal direction.

In this case, the IP can be largely inclined by the front-back inverting portion. Thus, the IP can be easily turned upside down.

A radiation image scanner according to a fifteenth aspect is the radiation image scanner according to any one of the first to fourteenth aspects, further including a stage moving mechanism that moves the stage between a setting position where the IP is set on the stage and a reading position where the photodetector reads the radiation image according to the excitation light from the excitation light source, in which the setting guide is provided at a position where the setting guide faces the stage located at the setting position.

Accordingly, it is easy to dispose the setting guide without interfering with the excitation light source and the photodetector.

The above description is illustrative in all aspects, and the present disclosure is not limited thereto. Innumerable modifications not illustrated can be envisaged without departing from the scope of the present disclosure.

While the invention has been shown and described in detail, the foregoing description is in all aspects illustrative and not restrictive. It is therefore understood that numerous modifications and variations can be devised without departing from the scope of the invention.

What is claimed is:

1. A radiation image scanner that reads a radiation image from a front surface of an imaging plate (IP), the radiation image scanner comprising:

a stage that supports the IP from a back surface side;

an excitation light source that irradiates the IP supported by the stage with excitation light;

a photodetector that detects light emitted from the IP by the excitation light; and a setting guide that guides the IP toward the stage, the setting guide including a first IP guide surface that guides the IP obliquely downward, the first IP guide surface being inclined downward, wherein at least one of the setting guide and the stage include a second IP guide surface being inclined downward, the second IP guide surface is a surface that is inclined downward to an opposite side with respect to the first IP guide surface, receives the IP guided by the first IP guide surface, and guides the IP obliquely downward, and at least one of the stage and the setting guide include a front-back inverting portion that inverts the IP in an inclined attitude identical to the second IP guide surface while coming into contact with the IP guided by the second IP guide surface from a front surface side of the IP.

2. The radiation image scanner according to claim 1, wherein the stage includes a supporting surface as the second IP guide surface, the supporting surface being inclined with respect to a horizontal direction and supporting the IP from a back surface side, the stage further includes a receiving surface that receives the IP supported by the supporting surface from a lower side in an inclination direction of the supporting surface, the first IP guide surface gradually slopes downward toward the supporting surface and guides the IP toward the supporting surface, the setting guide includes the front-back inverting portion, and the front-back inverting portion is a portion located closer to the supporting surface than an imaginary extension directly above a position where the receiving surface receives the IP.

3. The radiation image scanner according to claim 1, wherein the setting guide includes the second IP guide surface and the front-back inverting portion.

4. The radiation image scanner according to claim 1, further comprising a housing that covers the stage, the excitation light source, the photodetector, at least the first IP guide surface and the front-back inverting portion of the setting guide, and the second IP guide surface.

5. The radiation image scanner according to claim 1, wherein the first IP guide surface includes a portion that is a curved surface protruding outward.

6. The radiation image scanner according to claim 1, wherein the first IP guide surface has a shape of one straight line or a combination of a plurality of straight lines when viewed along a horizontal direction orthogonal to a guiding direction of the IP.

7. The radiation image scanner according to claim 1, wherein the front-back inverting portion is continuous to a downstream side of a guiding direction of the IP with respect to the first IP guide surface.

8. The radiation image scanner according to claim 1, wherein the setting guide further includes a restricting guide surface for the second IP guide surface that gradually approaches the second IP guide surface as the restricting guide surface goes downward in an inclination direction of the second IP guide surface.

9. The radiation image scanner according to claim 8, wherein the restricting guide surface is continuous to a downstream side of the front-back inverting portion.

10. The radiation image scanner according to claim 1, wherein the setting guide further includes an insertion guide positioned away from an upper end of the first IP guide surface by a distance corresponding to a thickness of the IP.

11. The radiation image scanner according to claim 1, wherein the setting guide further includes a recess that is located halfway of a guide path of the IP by the first IP guide surface and suppresses a flow of liquid along a guiding direction of the IP.

12. The radiation image scanner according to claim 1, wherein at least a part of the setting guide is detachably supported such that at least a part of the first IP guide surface is exposed outside while being in a detached state.

13. The radiation image scanner according to claim 1, wherein the setting guide further includes an insertion port through which the IP is inserted at an upper end of the first IP guide surface and a shutter that openably closes the insertion port.

14. The radiation image scanner according to claim 1, wherein the setting guide guides the IP in a posture in which a longitudinal direction of the IP is set along a moving direction of the IP in the first IP guide surface, and the stage supports the longitudinal direction of the IP in a posture in which the longitudinal direction of the IP is inclined with respect to a horizontal direction.

15. The radiation image scanner according to claim 1, further comprising a stage moving mechanism that moves the stage between a setting position where the IP is set on the stage and a reading position where the photodetector reads the radiation image according to the excitation light from the excitation light source, wherein the setting guide is provided at a position where the setting guide faces the stage located at the setting position.

16. The radiation image scanner according to claim 15, wherein the stage moving mechanism includes a motor that applies driving force to move the stage and a stage guide that guides the stage.

17. A setting guide that guides an imaging plate (IP) toward a stage that supports the IP from a back surface side, comprising:

a first IP guide surface that guides the IP obliquely downward, the first IP guide surface being inclined downward;

a second IP guide surface being inclined downward, the second IP guide surface being a surface that is inclined downward to an opposite side with respect to the first IP guide surface, receives the IP guided by the first IP guide surface, and guides the IP obliquely downward, and a front-back inverting portion that inverts the IP in an inclined attitude identical to the second IP guide surface while coming into contact with the IP guided by the second IP guide surface from a front surface side of the IP.

18. A radiation image scanner that reads a radiation image from a front surface of an imaging plate (IP), the radiation image scanner comprising:

a stage that supports the IP from a back surface side;

an excitation light source that irradiates the IP supported by the stage with excitation light;

a photodetector that detects light emitted from the IP by the excitation light; and a first IP guide surface that guides the IP obliquely downward, the first IP guide surface being inclined downward, wherein the stage includes a second IP guide surface being inclined downward, the second IP guide surface is a surface that is inclined downward to an opposite side with respect to the first IP guide surface, receives the IP guided by the first IP guide surface, and guides the IP obliquely downward, and the stage includes a front-back inverting portion that inverts the IP in an inclined attitude identical to the second IP guide surface while coming into contact with the IP guided by the second IP guide surface from a front surface side of the IP.

* * * * *